(12) United States Patent
Suh et al.

(10) Patent No.: US 10,743,774 B2
(45) Date of Patent: Aug. 18, 2020

(54) ASSESSMENT OF A VESSEL

(71) Applicant: ACIST Medical Systems, Inc., Eden Prairie, MN (US)

(72) Inventors: Jung W. Suh, Palo Alto, CA (US); Todd Suchecki, Robbinsdale, MN (US); Thomas M. Snyder, Saint Paul, MN (US); Robert F. Wilson, Roseville, MN (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 0 days.

(21) Appl. No.: 16/185,754

(22) Filed: Nov. 9, 2018

(65) Prior Publication Data

US 2019/0320911 A1 Oct. 24, 2019

Related U.S. Application Data

(60) Provisional application No. 62/660,521, filed on Apr. 20, 2018.

(51) Int. Cl.
*A61B 5/021* (2006.01)
*A61B 5/02* (2006.01)
(Continued)

(52) U.S. Cl.
CPC .......... *A61B 5/02007* (2013.01); *A61B 5/026* (2013.01); *A61B 5/02158* (2013.01); *A61B 5/02* (2013.01); *A61B 5/021* (2013.01)

(58) Field of Classification Search
CPC ........ A61B 5/02; A61B 5/021; A61B 5/02007
See application file for complete search history.

(56) References Cited

U.S. PATENT DOCUMENTS 3,738,356 A 6/1973 Workman
4,006,735 A 2/1977 Hittman et al.
(Continued)

FOREIGN PATENT DOCUMENTS

CN 1829466 A 9/2006
CN 203458373 U 3/2014
(Continued)

OTHER PUBLICATIONS

International Patent Application No. PCT/US2018/060047, International Search Report and Written Opinion dated Mar. 1, 2019, 14 pages.
(Continued)

*Primary Examiner* — Puya Agahi
(74) *Attorney, Agent, or Firm* — Fredrikson & Byron, P.A.

(57) ABSTRACT

One method for assessing a vessel can include obtaining a set of first location pressure measurements at a first location in the vessel over a first time period and a set of second location pressure measurements at a second location in the vessel over the first time period. This method can further include identifying a first leading characteristic associated with one or more pressure measurements in the set of first location pressure measurements, a second leading characteristic associated with one or more pressure measurements in the set of second location pressure measurements, a first trailing characteristic associated with one or more pressure measurements in the set of first location pressure measurements, and a second trailing characteristic associated with one or more pressure measurements in the set of second location pressure measurements. And, this method can include calculating a pressure ratio using pressure measurements between the identified characteristics.

20 Claims, 10 Drawing Sheets

(51) Int. Cl.
*A61B 5/026* (2006.01)
*A61B 5/0215* (2006.01)

(56) References Cited

U.S. PATENT DOCUMENTS

| | | |
|---|---|---|
| 4,771,782 A | 9/1988 | Millar et al. |
| 4,850,358 A | 7/1989 | Millar |
| 4,901,731 A | 2/1990 | Millar |
| 4,928,693 A | 5/1990 | Goodin et al. |
| 4,966,148 A | 10/1990 | Millar et al. |
| 4,991,590 A | 2/1991 | Shi |
| 5,046,497 A | 9/1991 | Millar et al. |
| 5,178,159 A | 1/1993 | Christian et al. |
| 5,228,452 A | 7/1993 | Samson |
| 5,280,786 A | 1/1994 | Wlodarczyk et al. |
| 5,395,311 A | 3/1995 | Andrews et al. |
| 5,533,957 A | 7/1996 | Aldea et al. |
| 5,597,377 A | 1/1997 | Aldea et al. |
| 5,715,827 A | 2/1998 | Corl et al. |
| 5,782,797 A | 7/1998 | Schweich, Jr. et al. |
| 5,800,397 A | 9/1998 | Wilson et al. |
| 5,938,624 A | 8/1999 | Akerfeldt et al. |
| 6,112,598 A | 9/2000 | Tenerz et al. |
| 6,146,354 A | 11/2000 | Beil et al. |
| 6,166,806 A | 12/2000 | Tjin et al. |
| 6,167,763 B1 | 1/2001 | Tenerz et al. |
| 6,196,980 B1 | 3/2001 | Akerfeldt et al. |
| 6,248,083 B1 | 6/2001 | Smith et al. |
| 6,295,990 B1 | 10/2001 | Lewis et al. |
| 6,471,656 B1 | 10/2002 | Shalman et al. |
| 6,615,667 B2 | 9/2003 | Smith |
| 6,733,459 B1 | 5/2004 | Atsumi |
| 6,852,261 B2 | 2/2005 | Benjamin |
| 6,868,736 B2 | 3/2005 | Sawatari et al. |
| 6,976,965 B2 | 12/2005 | Corl et al. |
| 7,134,994 B2 | 11/2006 | Alpert et al. |
| 7,329,223 B1 | 2/2008 | Ainsworth et al. |
| 7,402,151 B2 | 7/2008 | Rosenman et al. |
| 7,458,938 B2 | 12/2008 | Patel et al. |
| 7,491,176 B2 | 2/2009 | Mann |
| 7,507,237 B2 | 3/2009 | Geistert |
| 8,298,156 B2 | 10/2012 | Manstrom et al. |
| 9,775,524 B2 | 10/2017 | Davies et al. |
| 2002/0043113 A1 | 4/2002 | Tulkki et al. |
| 2002/0072647 A1 | 6/2002 | Schock et al. |
| 2002/0072679 A1 | 6/2002 | Schock et al. |
| 2003/0216621 A1 | 11/2003 | Alpert et al. |
| 2004/0168519 A1 | 9/2004 | Kalvensten et al. |
| 2005/0065511 A1 | 3/2005 | Geistert |
| 2005/0234428 A1 | 10/2005 | Spohn et al. |
| 2006/0133715 A1 | 6/2006 | Belleville et al. |
| 2007/0078352 A1 | 4/2007 | Pijls |
| 2007/0255145 A1 | 11/2007 | Smith et al. |
| 2008/0119758 A1 | 5/2008 | Samuelsson et al. |
| 2010/0234698 A1 | 9/2010 | Manstrom et al. |
| 2010/0241008 A1 | 9/2010 | Belleville et al. |
| 2013/0046190 A1* | 2/2013 | Davies ............... A61B 5/742 600/486 |
| 2013/0131523 A1* | 5/2013 | Suchecki .......... A61B 5/02007 600/486 |
| 2013/0190633 A1 | 7/2013 | Dorando et al. |
| 2014/0024950 A1 | 1/2014 | Hiltner et al. |
| 2015/0133799 A1* | 5/2015 | O'Connell ........... A61B 5/0215 600/486 |
| 2016/0206214 A1 | 7/2016 | Davies et al. |
| 2018/0280088 A1* | 10/2018 | Davies ................. A61B 5/743 |
| 2018/0344173 A1* | 12/2018 | Tu .................... A61B 5/02007 |

FOREIGN PATENT DOCUMENTS

| | | |
|---|---|---|
| EP | 1419796 B1 | 3/2008 |
| JP | H03032640 A | 2/1991 |
| JP | H03505822 A | 12/1991 |
| JP | H11188010 A | 7/1999 |
| JP | H11244248 A | 9/1999 |
| JP | 2000504249 A | 4/2000 |
| JP | 2002513605 A | 5/2002 |
| JP | 2003525067 A | 8/2003 |
| JP | 2004528920 A | 9/2004 |
| JP | 2004357985 A | 12/2004 |
| JP | 2005131421 A | 5/2005 |
| JP | 2005270425 A | 10/2005 |
| JP | 2005291945 A | 10/2005 |
| JP | 2006509547 A | 3/2006 |
| JP | 2008514308 A | 5/2008 |
| JP | 2009502432 A | 1/2009 |
| JP | 2012501807 A | 1/2012 |
| RU | 47203 U1 | 8/2005 |
| SU | 1802695 A3 | 3/1993 |
| WO | 9607351 A1 | 3/1996 |
| WO | 2010030882 A1 | 3/2010 |
| WO | 2011161212 A1 | 12/2011 |
| WO | 2014084377 A1 | 6/2014 |
| WO | 2017013020 A1 | 1/2017 |

OTHER PUBLICATIONS

Ashtekar et al., "In vitro quantification of guidewire flow-obstruction effect in model coronary stenosis for Interventional diagnostic procedure," Journal of Medical Devices, vol. 1, Sep. 2007, pp. 185-196.

FISO Technologies, Inc., Brochure (Product Data Sheet) for "FOP-MIV Pressure Sensor," downloaded from http://www.fiso.com on Aug. 29, 2008, 2 pages.

Gould et al., "Experimental Validation of Quantitative Coronary Arteriography for Determining Pressure-Flow Characteristics of Coronary Stenosis," Circulation, vol. 66, No. 5, Nov. 1982, pp. 930-937.

Hennigan et al., "Discordance Between Resting and Hyperemic Indices of Coronary Stenosis Severity," Circulation: Cardiovascular Interventions, vol. 9, No. 11, Nov. 2016, 9 pages.

Li et al., "Optical MEMS pressure sensor based on Fabry-Perot interferometry," Optics Express, Feb. 20, 2006, pp. 1497-1504.

Opsens Inc., Brochure (Product Data Sheet) entitled, "Fiber Optic Miniature Physiological Pressure Sensor OPP-M, MEMS-based Fiber Optic Pressure Sensor for Life Science Applications," downloaded from http://www.opsens.com on Aug. 29, 2008, 2 pages.

Pijls et al., "Coronary pressure measurement to assess the hemodynamic significance of serial stenoses within one coronary artery: validation in humans," Circulation, Nov. 2000, vol. 102, No. 19, pp. 2371-2377.

Pijls et al., "Measurement of Fractional Flow Reserve to Assess the Functional Severity of Coronary-Artery Stenosis," The New England Journal of Medicine, Sep. 12, 2008, pp. 1703-1708.

Roy et al., "Delineating the guide-wire flow obstruction effect in assessment of fractional flow reserve and coronary low reserve measurements," AJP: Heart and Circulatory Physiology, vol. 289, No. 1, Jul. 1, 2005, pp. H392-H397.

Sauser et al., "Pressure Microsensing Catheters for Neonatal Care," Proceedings of IEEE Sensors, 3, Art. No. W3L-A.1, 2004, pp. 1476-1479.

Sen et al., "Development and validation of a new adenosine-independent index of stenosis severity from coronary wave-intensity analysis: results of the ADVISE (ADenosine Vasodilator Independent Stenosis Evaluation) study," Journal of the American College of Cardiology, vol. 59, No. 15, Apr. 2012, pp. 1392-1402.

Serruys, MD, PhD et al., "Intracoronary Pressure and Flow Velocity with Sensor-Tip Guidewires: A New Methodological Approach for Assessment of Coronary Hemodynamics Before and After Coronary Interventions," The American Journal of Cardiology, vol. 71, No. 14, May 20, 1993, pp. D41-D53.

Tabbara et al., "Potential of intraluminal ultrasound for antioplasty guidance," Proceedings of SPIE—The International Society for Optical Engineering, 1201, 1990, pp. 523-526.

Van'T Veer et al., "Comparison of Different Diastolic Resting Indexes to iFR," Journal of the American College of Cardiology, vol. 70, No. 25, 2017, pp. 3088-3096.

(56) References Cited

OTHER PUBLICATIONS

Roy et al., "Guidewire flow obstruction effect on pressure drop-flow relationship in moderate coronary artery stenosis," Journal of Biomechanics, vol. 39, No. 5, Jan. 1, 2006, pp. 853-864.

* cited by examiner

ASSESSMENT OF A VESSEL

RELATED APPLICATION

This application claims the benefit of U.S. Provisional Application No. 62/660,521 filed Apr. 20, 2018, the contents of which are hereby incorporated by reference.

TECHNICAL FIELD

This disclosure relates generally to the field of medical technology and, more particularly, to devices, systems, and methods for assessing anatomical structures of patients, such as a constriction, or narrowing, at a location of interest in a blood vessel.

BACKGROUND

To better understand the severity of a particular condition at an anatomical structure of a patient, physiological data can be gathered and used to guide treatment decisions. One example of such a condition is a constriction, or narrowing, of a blood vessel, referred to, in some cases, as a stenosis. By gauging the severity of the constriction, appropriate treatment options can be determined.

One technique for evaluating the degree to which a stenosis obstructs flow through a blood vessel is called the Fractional Flow Reserve measurement (FFR). To calculate FFR for a given vessel, two blood pressure readings are taken—one on the distal side of the stenosis (e.g., downstream from the stenosis) and the other on the proximal, or aortic, side of the stenosis (e.g., upstream from the stenosis, toward the aorta). FFR is defined as the ratio of maximal blood flow in a stenotic artery, taken distal to the stenosis, to normal maximal flow, and is typically calculated based on a measured pressure gradient of the distal pressure to the proximal pressure. The pressure gradient across a stenosis may serve as an indicator of the severity of the stenosis. The more restrictive the stenosis is, the greater the pressure drop, and the lower the resulting FFR. FFR measurement may be a useful diagnostic tool. A physician might decide, for example, to perform an interventional procedure (e.g., angioplasty or stent placement) when FFR for a given stenosis is below a clinical threshold (e.g., 0.8), and may decide to forego such treatment for a given stenosis where FFR is above the clinical threshold (e.g., 0.8). Thus, FFR measurement can be a decision point for guiding treatment.

However, accurate assessment of the pressure drop at a stenosis generally requires that coronary resistance be stable and minimized. In traditional FFR, this has generally been achieved by inducing maximal hyperemia in the vessel through administration of a pharmacological hyperemic agent, such as adenosine. It would be preferable to make an approximation of FFR under normal flow conditions without needing to administer a pharmacological agent since this could reduce patient side effects as well as cost and time associated with the diagnostic assessment.

Techniques have recently been developed to make an approximation of FFR at a time when coronary resistance is naturally minimized and thus a pharmacological agent is not needed. These techniques have focused on identifying the diastole period of the cardiac cycle and taking pressure measurements during a defined sub-period of diastole when resistance has been empirically shown to be low. But, in order to identify the diastole period, these techniques rely on first identifying the dicrotic notch in the pressure measurements. The dicrotic notch represents closure of the aortic valve at the onset of ventricular diastole and appears in the pressure waveform as a relatively slight, upward deflection in a descending portion of the pressure waveform. However, depending on the particular patient, the dicrotic notch can be difficult to detect and, in some cases, there may be no discernable dicrotic notch at all. Since these FFR approximation techniques define the pressure measurement period relative to the dicrotic notch, failure to accurately identify the dicrotic notch can lead to use of pressure measurements taken when vessel resistance is material and thus result in an inaccurate approximation of FFR. This, in turn, may reduce the value of the FFR approximation in guiding treatment.

SUMMARY

Exemplary embodiments are described herein for assessing a vessel or other pertinent anatomical structure (e.g., a valve) of a patient. Various embodiments described herein can be useful in providing an approximation of Fractional Flow Reserve (FFR) that may serve as a reliable decision point for guiding treatment decisions since the provided approximation can be comparable to traditional FFR. Yet, certain embodiments can provide this approximation of FFR, for example, under normal flow conditions without inducing hyperemia (e.g., without administering a hyperemic pharmacological agent) and/or without needing to identify the dicrotic notch. Embodiments disclosed herein can identify characteristics, other than the dicrotic notch, associated with pressure measurements obtained not during hyperemia and use these identified characteristics to select pressure measurements taken at a time when vessel resistance is naturally minimized. Accordingly, such embodiments may be able to reduce patient side effects, as well as the cost and time, associated with inducing hyperemia while providing a more consistent and accurate approximation of FFR by eliminating the need to identify the dicrotic notch.

One exemplary embodiment includes a method for assessing a vessel. In this exemplary embodiment, the method includes obtaining a set of first location pressure measurements at a first location in the vessel over a first time period and a set of second location pressure measurements at a second location in the vessel over the first time period. The second location is different than the first location. For example, the first location can be one of distal to a location of interest and proximal to the location of interest while the second location can be the other of distal to the location of interest and proximal to the location of interest. The set of first location pressure measurements and the set of second location pressure measurements can be obtained not during hyperemia (i.e. a non-hyperemic state).

This method embodiment further includes identifying a first leading characteristic associated with one or more pressure measurements in the set of first location pressure measurements and a second leading characteristic associated with one or more pressure measurements in the set of second location pressure measurements.

This method embodiment also includes identifying a first trailing characteristic associated with one or more pressure measurements in the set of first location pressure measurements and a second trailing characteristic associated with one or more pressure measurements in the set of second location pressure measurements. The identified first trailing characteristic is after the identified first leading characteristic in the first time period and the identified second trailing characteristic is after the identified second leading characteristic in the first time period. Moreover, at least one of the identified first leading characteristic, the identified second leading characteristic, the identified first trailing characteristic, and the identified second trailing characteristic is associated with a pressure measurement in the respective set of first location pressure measurements and second location pressure measurements that is obtained without reference to any dicrotic notch that may be present in the respective set of first location pressure measurements and second location pressure measurements.

In addition, this method embodiment includes calculating a numerical value based on i) a pressure measurement in the set of first location pressure measurements between the identified first leading characteristic and the identified first trailing characteristic and ii) a pressure measurement in the set of second location pressure measurements between the identified second leading characteristic and the identified second trailing characteristic. For example, this method can include calculating a pressure ratio using i) a pressure measurement in the set of first location pressure measurements between the identified first leading characteristic and the identified first trailing characteristic and ii) a pressure measurement in the set of second location pressure measurements between the identified second leading characteristic and the identified second trailing characteristic. This method may further include providing the numerical value as an assessment of a restriction in the blood vessel.

Another exemplary embodiment includes a non-transitory computer-readable storage article having computer-executable instructions stored thereon. In this embodiment, the computer-executable instructions cause at least one programmable processor to receive a set of first location pressure measurements taken at a first location in a vessel over a first time period and a set of second location pressure measurements taken at a second location in the vessel over the first time period. The second location is different than the first location. And, the set of first location pressure measurements and the set of second location pressure measurements are taken not during hyperemia (i.e. a non-hyperemic state).

In this article embodiment, the computer-executable instructions further cause at least one programmable processor to identify a first leading characteristic associated with one or more pressure measurements in the set of first location pressure measurements and a second leading characteristic associated with one or more pressure measurements in the set of second location pressure measurements.

In this article embodiment, the computer-executable instructions also cause at least one programmable processor to identify a first trailing characteristic associated with one or more pressure measurements in the set of first location pressure measurements and a second trailing characteristic associated with one or more pressure measurements in the set of second location pressure measurements. The first trailing characteristic is after the first leading characteristic in the first time period and the second trailing characteristic is after the second leading characteristic in the first time period. Moreover, at least one of the identified first leading characteristic, the identified second leading characteristic, the identified first trailing characteristic, and the identified second trailing characteristic is associated with a pressure measurement in the respective set of first location pressure measurements and second location pressure measurements that is obtained without reference to any dicrotic notch that may be present in the respective set of first location pressure measurements and second location pressure measurements.

In this article embodiment, the computer-executable instructions additionally cause at least one programmable processor to calculate a pressure ratio using i) a pressure measurement in the set of first location pressure measurements between the first leading characteristic and the first trailing characteristic and ii) a pressure measurement in the set of second location pressure measurements between the second leading characteristic and the second trailing characteristic.

In these exemplary embodiments noted above, the identified characteristics can be any one or more of a variety of characteristic types. For example, the identified first leading characteristic, the identified second leading characteristic, the identified first trailing characteristic, and/or the identified second trailing characteristic can be a characteristic type selected from the group of characteristic types consisting of: a maximum pressure measurement, a minimum pressure measurement, a maximum decreasing pressure measurement rate of change, and a maximum increasing pressure measurement rate of change. In some cases all identified characteristics can be of the same characteristic type, but in other cases two or more different characteristic types can be identified.

The details of one or more examples are set forth in the accompanying drawings and the description below. Other features, objects, and advantages will be apparent from the description and drawings.

BRIEF DESCRIPTION OF DRAWINGS

The following drawings are illustrative of particular embodiments of the present invention and therefore do not limit the scope of the invention. The drawings are intended for use in conjunction with the explanations in the following description. Embodiments of the invention will hereinafter be described in conjunction with the appended drawings, wherein like numerals denote like elements.

FIG. 5 illustrates an exemplary embodiment where a minimum pressure measurement characteristic type is identified.

FIG. 6 illustrates an exemplary embodiment where a maximum decreasing pressure measurement rate of change characteristic type is identified.

FIG. 7 illustrates an exemplary embodiment where a maximum increasing pressure measurement rate of change characteristic type is identified.

FIG. 8 illustrates an exemplary embodiment where a threshold decreasing pressure measurement rate of change characteristic type is identified.

DETAILED DESCRIPTION

The following detailed description is exemplary in nature and provides some practical illustrations and examples. Those skilled in the art will recognize that many of the noted examples have a variety of suitable alternatives that are to be considered within the scope of the present disclosure.

Figure 1:
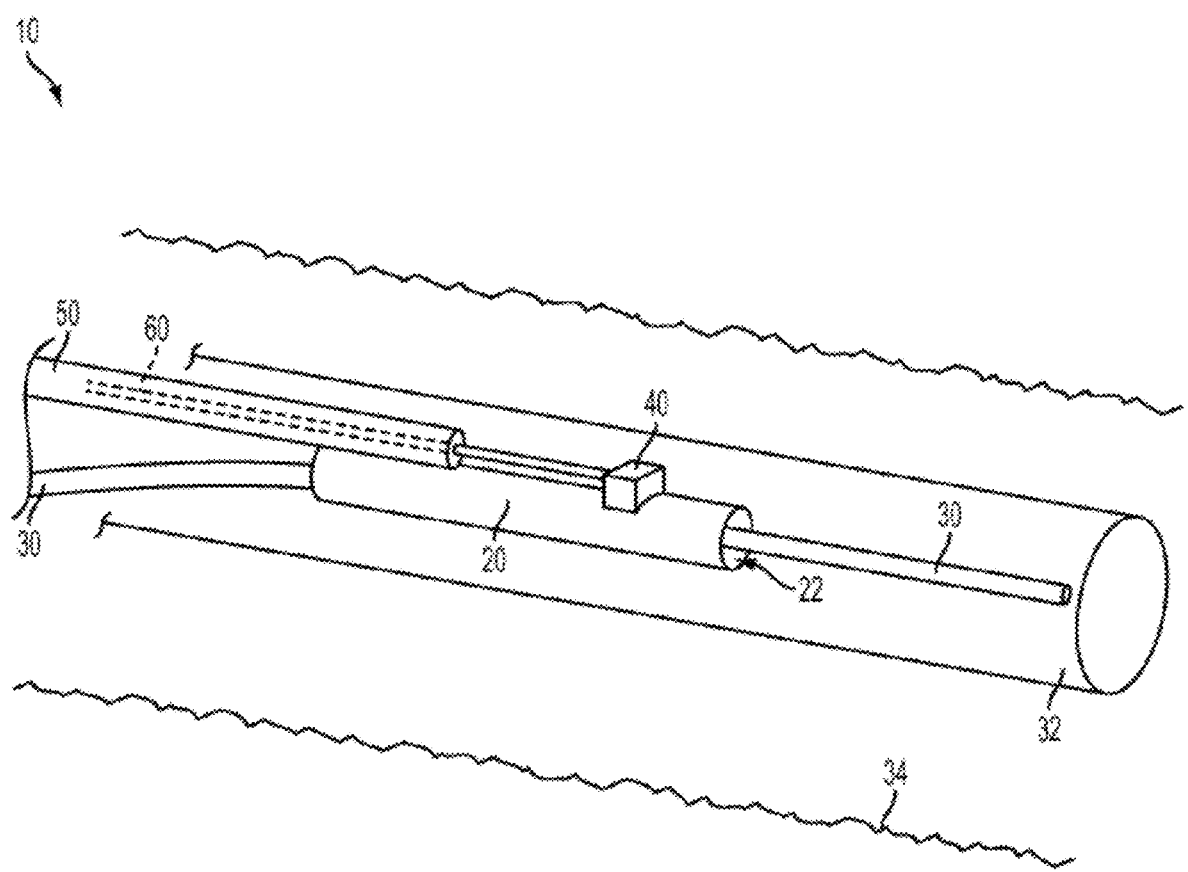
FIG. 1 is a perspective view of an exemplary embodiment of a sensor delivery device.

FIG. 1 illustrates a perspective view of an exemplary embodiment of a sensor delivery device 10 that can be used to gather one or more physiological parameters at a location of interest. The sensor delivery device 10 includes a distal sleeve 20 having a guidewire lumen 22 for slidably receiving a medical guidewire 30. A sensor 40 is coupled to the distal sleeve 20, sensor 40 being configured to sense a physiological parameter of a patient and generate a signal representative of that physiological parameter, for instance pressure. The distal sleeve 20, and hence, the sensor 40, may be positioned within a patient (e.g., within an anatomical structure of a patient, such as within a vein, artery, or other blood vessel, or across a heart valve) by causing the distal sleeve 20 to slide over the medical guidewire 30 to the desired position. In some cases, such as the example shown here, the device 10 is deployed using a guiding catheter 32. The guiding catheter 32 can be placed within a blood vessel 34, which could be, for example, a coronary artery of the patient. The device 10 and the guidewire 30 can then be manipulated inside the guiding catheter 32. For example, the sensor 40 can be positioned in the blood vessel 34 distal to a location of interest in the blood vessel 34 and used thereat to measure pressure during the cardiac cycle.

The sensor delivery device 10 of FIG. 1 also includes a proximal portion 50. The proximal portion 50 can be coupled to the distal sleeve 20 as shown here. The proximal portion 50 includes a communication channel 60 for communicating the signal from the sensor 40 to a location outside of the patient (e.g., to a processor, display, computer, monitor, or to another medical device). Communication channel 60 may comprise a fiber optic communication channel in certain embodiments, such as where the sensor 40 is a fiber optic pressure sensor. Alternately, communication channel 60 may comprise an electrically conductive medium, such as one or more electrical conducting wires. Of course, many other forms of communication media may be suitable for transmitting the signal generated by sensor 40 to a location outside of the patient.

The proximal portion 50 can be adapted to assist an operator (e.g., a physician or other medical staff) in positioning the distal sleeve 20 and the sensor 40 within an anatomical (e.g., vascular) structure of the patient. This is typically accomplished by an operator first inserting the guidewire 30 into a patient's vasculature and advancing it past an area of interest. The sensor delivery device 10 is then deployed by "threading" the distal sleeve 20 onto the guidewire 30 such that the lumen 22 slides over the guidewire 30 and advancing the distal sleeve 20 (and the associated sensor 40) by moving (e.g., pushing and/or pulling) the proximal portion 50 until sensor 40 is in the desired location relative to the location of interest in the blood vessel 34.

One diagnostic application for which the sensor delivery device 10 may be suited is the approximation of Fractional Flow Reserve (FFR) in the blood vessel 34 or other appropriate anatomical structure, such as a valve. In this application, the device 10 can be deployed at one or more locations of interest in the blood vessel 34 and the sensor 40 can be configured to measure pressure at the one or more locations of interest. In one example, the sensor 40 may be positioned to measure distal pressure, $P_d$, at a location downstream of a location of interest having a restriction (e.g., a stenosis) in the blood vessel 34. In a further example, the sensor 40 may then be positioned to measure aortic pressure, $P_a$, at a location upstream of the location of interest having the restriction (e.g., the stenosis) in the blood vessel 34. The use of the terms "downstream" and "upstream" are with respect to the normal direction of blood flow D, as shown in FIG. 1.

In some examples, the device 10 can include a second sensor spaced from the sensor 40 sufficiently so as to span a stenosis. In other examples, a second pressure sensor can be used that is separate from the distal sleeve 20 and proximal portion 50. For instance, in one example a second sensor can be separate from the device 10 and used to measure aortic pressure, $P_a$, at the location upstream of the location of interest having the restriction (e.g., the stenosis) in the blood vessel 34. These examples can provide the ability to obtain pressure measurements on each side of the stenosis without having to reposition the device 10.

Whether one or multiple sensors are used, a set of first location pressure measurements can be taken at a first location in the vessel over a first time period and a set of second location pressure measurements can be taken at a second, different location in the vessel over the first time period. This could also apply to anatomical structures of interest other than a vessel.

Figure 2:
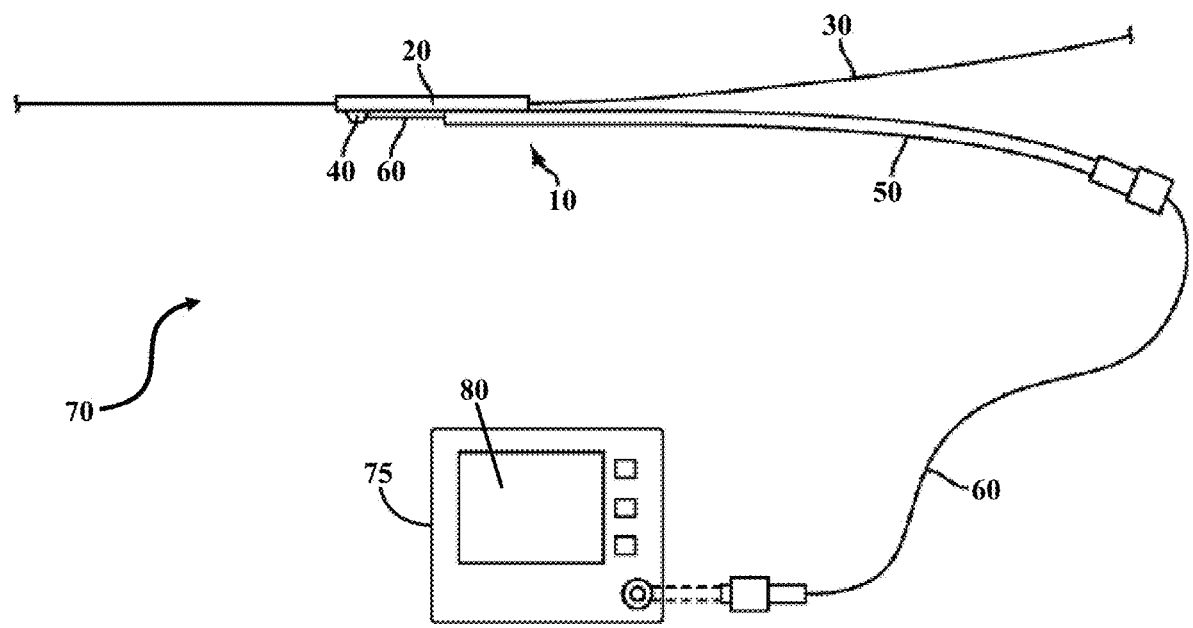
FIG. 2 is a diagram of an exemplary embodiment of a system for assessing the severity of a restriction at a location of interest in a vessel using the sensor delivery device of FIG. 1.

FIG. 2 shows a diagram of an exemplary embodiment of a system 70 for assessing the severity of a restriction at a location of interest in a vessel. The system 70 includes the sensor delivery device 10, as detailed in reference to FIG. 1, as well as a computing device 75. The computing device 75 can be connected to the sensor 40 such as via the communication channel 60, so as to receive one or more signals generated by the sensor 40 representative of a physiological parameter in the vessel (e.g., pressure). The computing device 75 can include one or more programmable processors as well as a non-transitory computer-readable storage article having computer-executable instructions stored thereon. The computer-executable instructions can cause at least one programmable processor to process signals from the sensor 40 (and any other sensor used in a particular application) and output information that can be useful in assessing the vessel. For example, these computer-executable instructions can cause at least one programmable processor to process signals from the sensor 40 (and any other sensor used in a particular application) to calculate a numerical value based on measured distal pressure, $P_d$, and measured aortic pressure, $P_a$ in the blood vessel and provide the numerical value as an assessment of a restriction in the blood vessel.

The computing device 75 can include a user interface 80. The one or more programmable processors can process the signal(s) from the sensor(s) and cause the user interface 80 to present a display of information related to the physiological parameter(s) measured within the vessel. Where the system 70 is used in an application to approximate FFR, the one or more programmable processors can process pressure signal(s) from the sensor(s), as described herein, and the user interface 80 can indicate a numerical approximation of FFR. In some such cases, the user interface 80 can present a display of a pressure waveform as a function of time for the aortic pressure, $P_a$, and/or a pressure waveform as a function of time for the distal pressure, $P_d$. The user interface 80 may also present addition useful information, such as navigational features and status information relating to the sensor delivery device 10 and/or patient.

As noted, the sensor delivery device 10 and system 70 can be used in assessing a vessel. In particular, the sensor delivery device 10 can be used to obtain a set of first location pressure measurements at a first location in the vessel over a first time period and a set of second location pressure measurements at a second, different location in the vessel over the first time period. For instance, where these sets of pressure measurements are used to approximate FFR, the first location can be on a first side of a stenosis in the vessel and the second location can be on a second, opposite side of the stenosis in the vessel as detailed above. Embodiments of techniques for using (e.g., processing) such sets of pressure measurements to approximate FFR are described as follows.

Proper assessment of stenosis severity generally requires that vessel resistance be minimized. In traditional FFR, this is achieved by inducing maximal hyperemia in the vessel through administration of a hyperemic pharmacological agent, such as adenosine, and then taking pressure measurements during the induced maximal hyperemia. Techniques, as well as devices, systems, and computer-executable instructions, disclosed herein can use pressure measurements taken in the vessel not during hyperemia (i.e. during a non-hyperemic state) and thus do away with administering a hyperemic pharmacological agent, or in some cases any type of pharmacological agent. Instead, these embodiments can identify characteristics associated with pressure measurements obtained not during hyperemia and use these identified characteristics to select pressure measurements at a time when vessel resistance is naturally minimized. These selected pressure measurements can then be used to calculate a pressure ratio. Since embodiments of techniques disclosed herein can use pressure measurements obtained not during hyperemia, the calculated pressure ratio can be referred to as an approximation of FFR. Though embodiments disclosed herein can provide certain advantages by eliminating the need for hyperemia (e.g., by administration of a hyperemic agent), it is to be understood that any of the embodiments disclosed herein can be used in a hyperemic state.

Figure 3A:
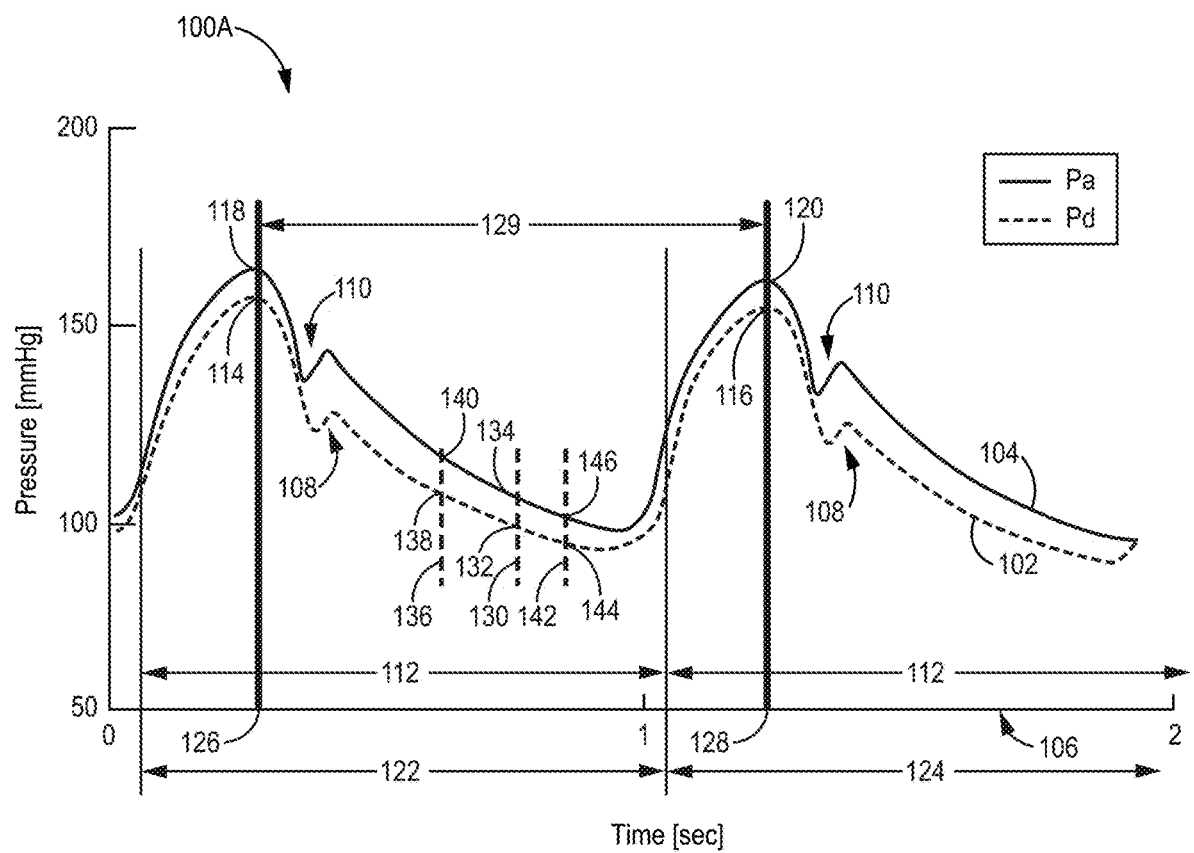
FIGS. 3A and 3B each show a graphical representation of pressure measurements that can be used to calculate a numerical value, such as a pressure ratio, according to one exemplary embodiment. In particular, FIGS. 3A and 3B each illustrate an exemplary embodiment where a maximum pressure measurement characteristic type is identified with FIG. 3B showing a particular aspect of this embodiment where independent characteristic identification is used.
Figure 3B:
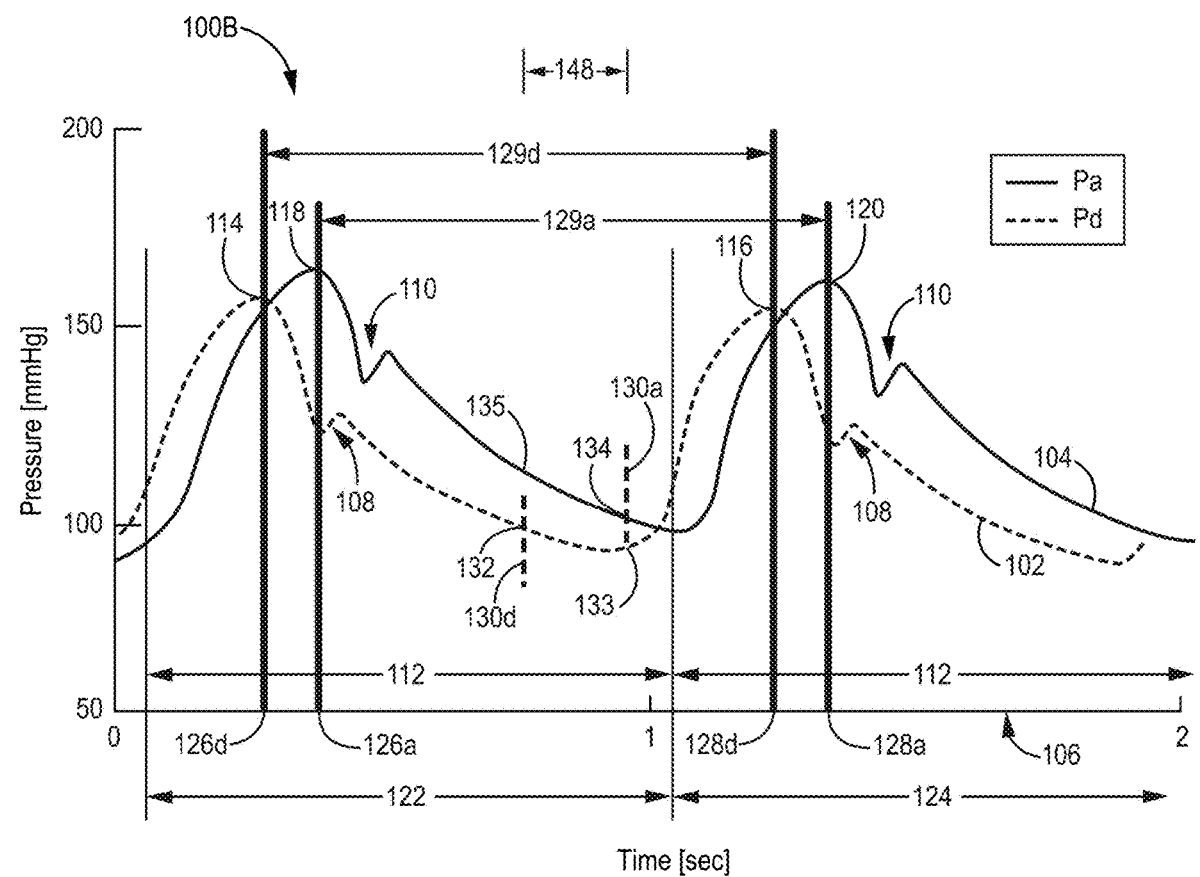

FIGS. 3A and 3B each show a graphical representation 100A, 100B of a set of first location pressure measurements 102 and a set of second location pressure measurements 104. The set of first location pressure measurements 102 can include a number of individual pressure measurements taken at a first location in the vessel over a first time period 106. The set of second location pressure measurements 104 can include a number of individual pressure measurements taken at a second, different location in the vessel taken over the same first time period 106. In one example, the set of first location pressure measurements 102 could be taken at a location distal to a region of interest (e.g., a restriction, such as a stenosis) and thus referred to as a distal pressure, $P_d$, while the set of second location pressure measurements 104 could be taken at a location proximal to, or in a direction toward the aorta from, the region of interest (e.g., the restriction, such as the stenosis) and thus referred to as the aortic pressure, $P_a$. The first time period 106 can represent a non-hyperemic state in the vessel such that the set of first location pressure measurements 102 and the set of second location pressure measurements 104 can be obtained not during hyperemia.

FIGS. 3A and 3B graphically show, for illustrative purposes, each of the set of first location pressure measurements 102 and the set of second location pressure measurements 104 as a pressure waveform as a function of the first time period 106. Though in certain embodiments of techniques within the scope of this disclosure, the set of first location pressure measurements 102 and the set of second location pressure measurements 104 can be used without needing to generate a graphical waveform, for instance in the form of numerical data sets, including individual measured pressures and corresponding times.

As shown in FIGS. 3A and 3B, the set of first location pressure measurements 102 includes a dicrotic notch 108 and the set of second location pressure measurements 104 includes a dicrotic notch 110. In the exemplary diagnostic application described herein, the dicrotic notches 108, 110 represent closure of the aortic valve at the onset of ventricular diastole during a cardiac cycle 112. Each dicrotic notch 108, 110 appears in the respective pressure waveform as a relatively slight, upward deflection in a descending portion of the pressure waveform. In other words, each dicrotic notch 108, 110 is represented by one or more increasing pressure measurements in the respective set of pressure measurements that has decreasing pressure measurements immediately before and immediately after the one or more increasing pressure measurements in time.

As described previously, past techniques for approximating FFR rely on identifying the diastole period of the cardiac cycle and using pressure measurements taken during a predefined sub-period of diastole, sometimes referred to as a "wave-free period," when vessel resistance has been empirically found to be low. In order to identify the beginning of the diastole period, these past techniques rely on identifying the dicrotic notch 108, 110 in each set of pressure measurements. Using the identified dicrotic notch 108, 110 as a reference point, these past techniques then define a sub-period within diastole relative to the dicrotic notch 108, 110 from which pressure measurements are to be used in calculating a pressure ratio. Because these past FFR approximation techniques define the period (e.g., diastole) from which pressure measurements are used relative to the dicrotic notch, failure to accurately identify the dicrotic notch in pressure measurements taken for a particular patient is problematic. Namely, it can lead to an inaccurate approximation of FFR since the pressure ratio may end up being calculated using pressure measurements taken when vessel resistance is material, and detrimental, to the pressure measurements.

FIGS. 3A and 3B show idealized waveforms for illustrative purposes, but in practice the dicrotic notch can be difficult to detect across many patients as a result of various anatomical conditions and, in some cases, there may be no detectable dicrotic notch at all. For instance, depending on the particular patient, the dicrotic notch may be accompanied by a number of other upward deflections in the descending portion of the pressure waveform. This makes it difficult to identify which such deflection is the dicrotic notch (e.g., which represents closure of the aortic valve), and which of the other deflections are merely noise associated with the particular patient's anatomy. In other instances, depending on the particular patient's anatomy, the descending portion of the pressure waveform may have no upward deflection and thus no detectable dicrotic notch.

Accordingly, various embodiments of techniques disclosed herein can identify characteristics associated with pressure measurements (e.g., obtained not during hyperemia) at a time other than when a dicrotic notch is present. For instance, the type of characteristic to be identified by techniques disclosed herein could include, as examples, one or more of a maximum pressure measurement, a minimum pressure measurement, a maximum or threshold decreasing pressure measurement rate of change, and a maximum increasing pressure measurement rate of change. The identified characteristics in these embodiments may be more readily and consistently identified across various patients as compared to the dicrotic notch. These embodiments can then use the identified characteristics to select pressure measurements relative thereto (e.g., one or more pressure measurements taken at times between the identified characteristics) and then use the selected pressure measurements to calculate a numerical value, such as a pressure ratio approximating FFR. For instance, the pressure measurements used in calculating the pressure ratio can be selected relative to the identified characteristics so that the selected pressure measurements are those taken at a time when vessel resistance has been shown to be naturally minimized. Accordingly, such embodiments may be able to reduce patient side effects as well as the cost and time associated with inducing hyperemia in traditional FFR while providing a more consistent and accurate approximation of FFR by eliminating the need to identify the dicrotic notch.

One exemplary embodiment of such a technique for calculating a pressure ratio to approximate FFR is described in reference to FIGS. 3A and 3B. In the exemplary embodiment described in reference to FIGS. 3A and 3B, the technique uses a maximum pressure measurement as the type of characteristic to be identified and used to select pressure measurements relative thereto for use in calculating a pressure ratio approximating FFR. This exemplary technique will be described in reference to FIG. 3A. Then, in reference to FIG. 3B, a particular aspect of independent characteristic identification for each of the set of first location pressure measurements 102 and the set of second location pressure measurements 104, that can be used in this exemplary technique, will be described.

For the set of first location pressure measurements 102, a first leading characteristic 114 and a first trailing characteristic 116 are identified. The identified first trailing characteristic 116 is after the identified first leading characteristic 114 in the first time period 106. The first leading characteristic 114 is associated with one or more pressure measurements in the set of first location pressure measurements 102 and the first trailing characteristic 116 is associated with one or more pressure measurements in the set of first location pressure measurements 102. The one or more pressure measurements in the set of first location pressure measurements 102 with which the first trailing characteristic 116 is associated can be different (e.g., taken at a different time) than the one or more pressure measurements in the set of first location pressure measurements 102 with which the first leading characteristic 114 is associated.

In particular, in the embodiment of the technique described in reference to FIGS. 3A and 3B, the first leading characteristic 114 and the first trailing characteristic 116 are characteristics identified as a maximum pressure measurement in the set of first location pressure measurements 102. In the example shown here, the first leading characteristic 114 is identified as a maximum pressure measurement in the set of first location pressure measurements 102 within a first predefined time interval 122 of the first time period 106. Also in the example shown here, the first trailing characteristic 116 is identified as a maximum pressure measurement in the set of first location pressure measurements 102 within a second predefined time interval 124 of the first time period 106 that is subsequent to the first predefined time interval 122. The first predefined time interval 122 and the second predefined time interval 124 can be set as appropriate for a specific application. In some examples, the first predefined time interval 122 and the second predefined time interval 124 will be set to be consecutive and equal in duration. In the example shown here, the first predefined time interval 122 is set to approximate the time it generally takes for one cardiac cycle 112 (e.g., of the particular patient in an application). The second predefined time interval 124 can similarly be set to approximate the time it generally takes for another, subsequent cardiac cycle 112.

The first leading characteristic 114 and the first trailing characteristic 116 are not associated with pressure measurements representing the dicrotic notch 108. Instead, each of the first leading characteristic 114 and the first trailing characteristic 116 is associated with one or more pressure measurements in the set of first location pressure measurements 102 that is obtained at a time (e.g., a time 126, a time 128) in the first time period 106 that differs from a time in the first time period 106 at which the dicrotic notch 108 is present in the set of first location pressure measurements 102.

For the set of second location pressure measurements 104, a second leading characteristic 118 and a second trailing characteristic 120 are identified. The identified second trailing characteristic 120 is after the identified second leading characteristic 118 in the first time period 106. The second leading characteristic 118 is associated with one or more pressure measurements in the set of second location pressure measurements 104 and the second trailing characteristic 120 is associated with one or more pressure measurements in the set of second location pressure measurements 104. The one or more pressure measurements in the set of second location pressure measurements 104 with which the second trailing characteristic 120 is associated can be different (e.g., taken at a different time) than the one or more pressure measurements in the set of second location pressure measurements 104 with which the second leading characteristic 118 is associated.

In particular, in the embodiment of the technique described in reference to FIGS. 3A and 3B, the second leading characteristic 118 and the second trailing characteristic 120 are characteristics identified as a maximum pressure measurement in the set of second location pressure measurements 104. In the example shown here, the second leading characteristic 118 can be identified as a maximum pressure measurement in the set of second location pressure measurements 104 within the first predefined time interval 122. Also in the example shown here, the second trailing characteristic 120 can be identified as a maximum pressure measurement in the set of second location pressure measurements 104 within the second predefined time interval 124. In some cases, an identified maximum pressure measurement may represent more than one individual pressure measurement in the set of first location pressure measurements 102 and/or the set of second location pressure measurements 104. For example, in either or both of these sets an identified maximum pressure measurement can be identified as corresponding to an average time in the respective predefined time interval that represents multiple consecutive localized pressure measurements that are a predetermined amount greater than other pressure measurements adjacent in time. This can be useful, in one example, in aligning identified leading and/or trailing characteristics from the different sets 102, 104 at a common time in the respective predefined time interval.

The second leading characteristic 118 and the second trailing characteristic 120 are not associated with pressure measurements representing the dicrotic notch 110. Instead, each of the second leading characteristic 118 and the second trailing characteristic 120 is associated with one or more pressure measurements in the set of second location pressure measurements 104 that is obtained at a time (e.g., a time 126, a time 128) in the first time period 106 that differs from a time in the first time period 106 at which the dicrotic notch 110 is present in the set of second location pressure measurements 104.

In some cases, as shown in FIG. 3A, the maximum pressure measurement identified as the first leading characteristic 114 and the maximum pressure measurement identified as the second leading characteristic 118 may be at a same time 126 in the first time period 106. Similarly, in some cases, as shown in FIG. 3A, the maximum pressure measurement identified as the first trailing characteristic 116 and the maximum pressure measurement identified as the second trailing characteristic 120 may be at a same time 128 in the first time period 106. Though, as will be described in reference to FIG. 3B, in other cases the maximum pressure measurement identified as the first leading characteristic 114 and the maximum pressure measurement identified as the second leading characteristic 118 may be at different times in the first time period 106 and the maximum pressure measurement identified as the first trailing characteristic 116 and the maximum pressure measurement identified as the second trailing characteristic 120 may be at different times in the first time period 106.

The identified leading and trailing characteristics can serve as references for selecting pressure measurements that are used to calculate a pressure ratio. For instance, a pressure measurement can be selected in the set of first location pressure measurements 102 between the identified first leading characteristic 114 and the identified first trailing characteristic 116. Likewise, a pressure measurement can be selected in the set of second location pressure measurements 104 between the identified second leading characteristic 118 and the identified second trailing characteristic 120. In one case, the selected pressure measurement between the identified first leading characteristic 114 and the identified first trailing characteristic 116 and the selected pressure measurement between the second leading characteristic 118 and the identified second trailing characteristic 120 can be obtained at the same time in the first time period 106. Then, a numerical value representing an assessment of a restriction in the blood vessel, such as a pressure ratio, can be calculated using i) the selected pressure measurement between the identified first leading characteristic 114 and the identified first trailing characteristic 116 and ii) the selected pressure measurement between the second leading characteristic 118 and the identified second trailing characteristic 120. In other instances, pressure measurements can be selected relative to the identified leading and trailing characteristics at locations other than between the identified leading and trailing characteristics.

For example, in some embodiments, two or more pressure measurements from each set between the respective identified characteristics can be used in calculating the pressure ratio. As one such example, one pressure measurement in the set of first location pressure measurements 102 between the identified first leading characteristic 114 and the identified first trailing characteristic 116 can be averaged with another pressure measurement in the set of first location pressure measurements 102 between the identified first leading characteristic 114 and the identified first trailing characteristic 116. Likewise, one pressure measurement in the set of second location pressure measurements 104 between the identified second leading characteristic 118 and the identified second trailing characteristic 120 can be averaged with another pressure measurement in the set of second location pressure measurements 104 between the identified second leading characteristic 118 and the identified second trailing characteristic 120. Then, the pressure ratio can be calculated using the averaged pressure measurements in the set of first location pressure measurements 102 between the identified first leading characteristic 114 and the identified first trailing characteristic 116 and the averaged pressure measurements in the set of second location pressure measurements 104 between the identified second leading characteristic 118 and the identified second trailing characteristic 120.

In some cases, one or more pressure measurements used to calculate the pressure ratio can be selected at a particular location between the respective leading and trailing characteristics. For example, the pressure ratio can be calculated using i) a pressure measurement 132 that is a first distance 130 (e.g., as measured in time and thus can be referred to as a time 130) between the identified first leading characteristic 114 and the identified first trailing characteristic 116 and ii) a pressure measurement 134 that is the first distance 130 (e.g., as measured in time and thus can be referred to as the time 130) between the identified second leading characteristic 118 and the identified second trailing characteristic 120. In the example illustrated in FIG. 3A, the first distance is 130 is midway between (e.g., as measured in time) the identified first leading characteristic 114 and the identified first trailing characteristic 116 and midway between (e.g., as measured in time) the identified second leading characteristic 118 and the identified second trailing characteristic 120. Thus, as shown here, the first distance 130 is fifty percent of the time 129 spanning between the time 126, associated with the respective leading characteristics 114, 118, and the time 128, associated with the respective trailing characteristics 116, 120.

In those embodiments noted previously where two or more pressure measurements from each set between the respective identified characteristics are used in calculating the pressure ratio, each of these two or more pressure measurements can also be selected at a particular location between the respective leading and trailing characteristics. In the example shown in FIG. 3A, in addition to using pressure measurements 132, 134 at the first distance 130, pressure measurements at a second distance 136 and/or pressure measurements at a third distance 142 can be used.

For instance, i) a pressure measurement 138 that is the second distance 136 between the identified first leading characteristic 114 and the identified first trailing characteristic 116 and ii) a pressure measurement 140 that is the second distance 136 between the identified second leading characteristic 118 and the identified second trailing characteristic 120 can each be used along with the pressure measurements 132, 134 to calculate a pressure ratio. The second distance 136 can be between the time 126 and the time at which the first distance 130 is set, for instance twenty percent, twenty five percent, thirty percent, thirty five percent, forty percent, or forty five percent of the time 129.

In addition, i) a pressure measurement 144 that is the third distance 142 between the identified first leading characteristic 114 and the identified first trailing characteristic 116 and ii) a pressure measurement 146 that is the third distance 142 between the identified second leading characteristic 118 and the identified second trailing characteristic 120 can each be used along with the pressure measurements 132, 134, and in addition to or as an alter to the pressure measurements 138, 140 calculate a pressure ratio. The third distance 142 can be between the time 128 and the time at which the first distance 130 is set, for instance fifty five percent, sixty percent, sixty five percent, seventy percent, seventy five percent, eighty percent, eighty five percent, or ninety percent of the time 129.

These two or more pressure measurements from each set at a particular location between the respective leading and trailing characteristics can be combined and used to calculate a pressure ratio. For example, the pressure measurement 132 can be averaged with the pressure measurement 138 and/or 144. Likewise, the pressure measurement 134 can be averaged with the pressure measurement 140 and/or 146. Then, the pressure ratio can be calculated using the averaged pressure measurements at the particular locations in the set of first location pressure measurements 102 between the identified first leading characteristic 114 and the identified first trailing characteristic 116 and the averaged pressure measurements at the particular locations in the set of second location pressure measurements 104 between the identified second leading characteristic 118 and the identified second trailing characteristic 120.

As noted, FIG. 3B illustrates an example of a particular aspect of independent characteristic identification for each of the set of first location pressure measurements 102 and the set of second location pressure measurements 104. Once one or more characteristics are independently identified in each of the set of first location pressure measurements 102 and the set of second location pressure measurements 104, these one or more characteristics can be used to select one or more pressure measurements in each of the set of first location pressure measurements 102 and the set of second location pressure measurements 104 and calculate a numerical value the same as, or similar to, that described elsewhere (e.g., with respect to FIG. 3A) herein. As in the example described in reference to FIG. 3A, in the example of FIG. 3B the first leading characteristic 114 and the first trailing characteristic 116 are characteristics identified as a maximum pressure measurement in the set of first location pressure measurements 102 and the second leading characteristic 118 and the second trailing characteristic 120 are characteristics identified as a maximum pressure measurement in the set of second location pressure measurements 104. Though any one or more of the aspects disclosed in reference to FIG. 3B can be used with any other characteristic types disclosed elsewhere herein (e.g., identification of any one or more characteristics disclosed in reference to FIGS. 4, 5, 6, 7, and 8).

In some examples, as shown in FIG. 3B, the pressure waveform representing the set of first location pressure measurements 102 may be offset, or shifted, in the first time period 106 relative to the pressure waveform representing the set of second location pressure measurements 104. This may occur, in certain exemplary applications, when the set of first location pressure measurements 102 and the set of second location pressure measurements 104 are obtained at different locations that experience pressure changes at different times due to the distance between these different locations.

In the example described in reference to FIG. 3B, the first leading characteristic 114 and the first trailing characteristic 116 are identified in the set of first location pressure measurements 102 independent of the second leading characteristic 118 and the second trailing characteristic 120 in the set of second location pressure measurements 104. As shown here, the first leading characteristic 114 is identified as a maximum pressure measurement in the set of first location pressure measurements 102 and the second leading characteristic 118 is identified as a maximum pressure measurement in the set of second location pressure measurements 104 within the first predefined time interval 122 of the first time period 106. Namely, the first leading characteristic 114 is identified as a maximum pressure measurement in the set of first location pressure measurements 102 at time 126d. The second leading characteristic 118 is identified as a maximum pressure measurement in the set of second location pressure measurements 104 at time 126a that is different than the time 126d. As also shown here, the first trailing characteristic 116 is identified as a maximum pressure measurement in the set of first location pressure measurements 102 and the second trailing characteristic 120 is identified as a maximum pressure measurement in the set of second location pressure measurements 104 within the second predefined time interval 124 of the first time period 106. Namely, the first trailing characteristic 116 is identified as a maximum pressure measurement in the set of first location pressure measurements 102 at time 128d. The second trailing characteristic 120 is identified as a maximum pressure measurement in the set of second location pressure measurements 104 at time 128a that is different than the time 128d.

As described previously, the first leading characteristic 114, the first trailing characteristic 116, the second leading characteristic 118, and the second trailing characteristic 120 are not associated with pressure measurements representing the respective dicrotic notch 108, 110.

In FIG. 3B, the identified leading and trailing characteristics can serve as references for selecting pressure measurements that are used to calculate a pressure ratio. For instance, a pressure measurement can be selected in the set of first location pressure measurements 102 between the identified first leading characteristic 114 and the identified first trailing characteristic 116. Likewise, a pressure measurement can be selected in the set of second location pressure measurements 104 between the identified second leading characteristic 118 and the identified second trailing characteristic 120.

As one example, shown in FIG. 3B, one or more pressure measurements used to calculate the pressure ratio can be selected at a particular location between the respective leading and trailing characteristics. For instance, the pressure ratio can be calculated using the pressure measurement 132 that is a first distance 130d (e.g., as measured in time and thus can be referred to as a time 130d) between the identified first leading characteristic 114 and the identified first trailing characteristic 116 and/or the pressure measurement 134 that is a first distance 130a (e.g., as measured in time and thus can be referred to as a time 130a) between the identified second leading characteristic 118 and the identified second trailing characteristic 120. As shown in the example of FIG. 3B, the first distance is 130d is midway between (e.g., as measured in time) the identified first leading characteristic 114 and the identified first trailing characteristic 116. Thus, as shown here, the first distance 130d is fifty percent of time 129d that spans between the time 126d, associated with the first leading characteristics 114, and the time 128d, associated with the first trailing characteristics 116. And, the first distance 130a is midway between (e.g., as measured in time) the identified second leading characteristic 118 and the identified second trailing characteristic 120. Thus, as shown here, the first distance 130a is fifty percent of time 129a that spans between the time 126a, associated with the second leading characteristics 116, and the time 128a, associated with the second trailing characteristics 120. Because in FIG. 3B the pressure waveform representing the set of first location pressure measurements 102 is offset in the first time period 106 relative to the pressure waveform representing the set of second location pressure measurements 104, the first distance 130a may be offset from the first distance 130d. As shown here, the first distance 130a is offset from the first distance 130d by a time 148.

The pressure ratio can be calculated using the pressure measurement 132 and/or the pressure measurement 134 in various ways. As one example, a pressure ratio can be calculated using i) the pressure measurement 132, in set of first location pressure measurements 102, at the time corresponding to 130d and ii) the pressure measurement 134, in set of second location pressure measurements 104, at the time corresponding to 130a. As another example, a pressure ratio can be calculated using i) the pressure measurement 132, in set of first location pressure measurements 102, at the time corresponding to 130d and ii) a pressure measurement 135, in the set of second location pressure measurements 104, at the time corresponding to 130d. Thus, in this example, the pressure measurement 132 can be identified using the leading and trailing characteristics 114 and 116, as described, and the pressure measurement 135 can then be identified as a pressure measurement in the set of second location pressure measurements 104 at the time in the first time period 106 corresponding to the pressure measurement 132. As a further example, a pressure ratio can be calculated using i) the pressure measurement 134, in the set of second location pressure measurements 104, at the time corresponding to 130a and ii) a pressure measurement 133, in the set of first location pressure measurements 102, at the time corresponding to 130a. Thus, in this example, the pressure measurement 134 can be identified using the leading and trailing characteristics 118 and 120, as described, and the pressure measurement 133 can then be identified as a pressure measurement in the set of first location pressure measurements 102 at the time in the first time period 106 corresponding to the pressure measurement 134.

In some instances where the pressure waveforms are offset, as in FIG. 3B, a correction factor can be applied to calculate a pressure ratio. For instance, in one example a pressure ratio can be calculated using i) the pressure measurement 132, in set of first location pressure measurements 102, at the time corresponding to 130d and ii) a corrected pressure measurement that is calculated by applying a correction factor to the pressure measurement 135, in the set of second location pressure measurements 104, at the time corresponding to 130d. The correction factor applied to the pressure measurement 135 can be a numerical multiplier (e.g., less than one or greater than one) that compensates the pressure measurement 135 for the offset in timing between the pressure waveforms for the first and second location pressure measurements 102, 104. In one case, the correction factor can be a numerical multiplier (e.g., less than one or greater than one) that compensates the pressure measurement 135 for the offset time 148. As such, in this case, the correction factor can be a numerical multiplier corresponding to the offset time 148 to adjust the pressure measurement 135 for this offset time 148. Thus, here, the greater the offset time 148, the greater the adjustment value of the correction factor applied to the pressure measurement 135.

In another correction factor example, a pressure ratio can be calculated using i) the pressure measurement 134, in set of second location pressure measurements 104, at the time corresponding to 130a and ii) a corrected pressure measurement that is calculated by applying a correction factor to the pressure measurement 133, in the set of first location pressure measurements 102, at the time corresponding to 130a. The correction factor applied to the pressure measurement 133 can be a numerical multiplier (e.g., less than one or greater than one) that compensates the pressure measurement 133 for the offset in timing between the pressure waveforms for the first and second location pressure measurements 102, 104. In one case, the correction factor can be a numerical multiplier (e.g., less than one or greater than one) that compensates the pressure measurement 133 for the offset time 148. As such, in this case, the correction factor can be a numerical multiplier corresponding to the offset time 148 to adjust the pressure measurement 133 for this offset time 148. Thus, here, the greater the offset time 148, the greater the adjustment value of the correction factor applied to the pressure measurement 133.

In certain examples, an electrocardiogram (sometimes abbreviated as ECG or EKG) can be used to help identify a leading and/or trailing characteristic in one or more sets of pressure measurements. One or both of the first and second location pressure waveforms can be compared to an electrocardiogram trace. Through this comparison, an ascertainable characteristic of the electrocardiogram trace can be used to identify a corresponding characteristic of one or both of the first and second location pressure waveforms. This may be useful when a particular characteristic of one or both of the first and second location pressure waveforms sought to be identified is difficult to identify in isolation. This may be the case, for example, in certain patients where two or more pressure measurements adjacent in time in a pressure waveform are near a similar, maximum pressure value. By comparing this pressure waveform to an electrocardiogram trace of the patient acquired at the same time as the pressure measurement, a readily ascertainable characteristic of an electrocardiogram trace can be used to determine which pressure measurement should be identified as the maximum pressure measurement characteristic.

For instance, an electrocardiogram can be used to identify a maximum pressure measurement as each of the leading and trailing characteristics. In this example, a time of a peak (sometimes referred to as an "R" wave or peak of ventricular contraction) of a first electrocardiogram trace can be determined. Then, this time of the peak of the first electrocardiogram trace can be used as the time at which a pressure measurement in the set (e.g., the set of first and/or second location pressure measurements) of pressure measurements is identified as a leading characteristic. Likewise, a time of a peak of a second, subsequent electrocardiogram trace can be determined. Then, this time of the peak of the second electrocardiogram trace can be used as the time at which a pressure measurement in the set (e.g., the set of first and/or second location pressure measurements) of pressure measurements is identified as a trailing characteristic.

In other examples, an electrocardiogram can be used to help identify other types of leading and/or trailing characteristic in one or more sets of pressure measurements. This can include, for example, the types of leading and trailing characteristics disclosed in reference to FIGS. 4-8.

Figure 4:
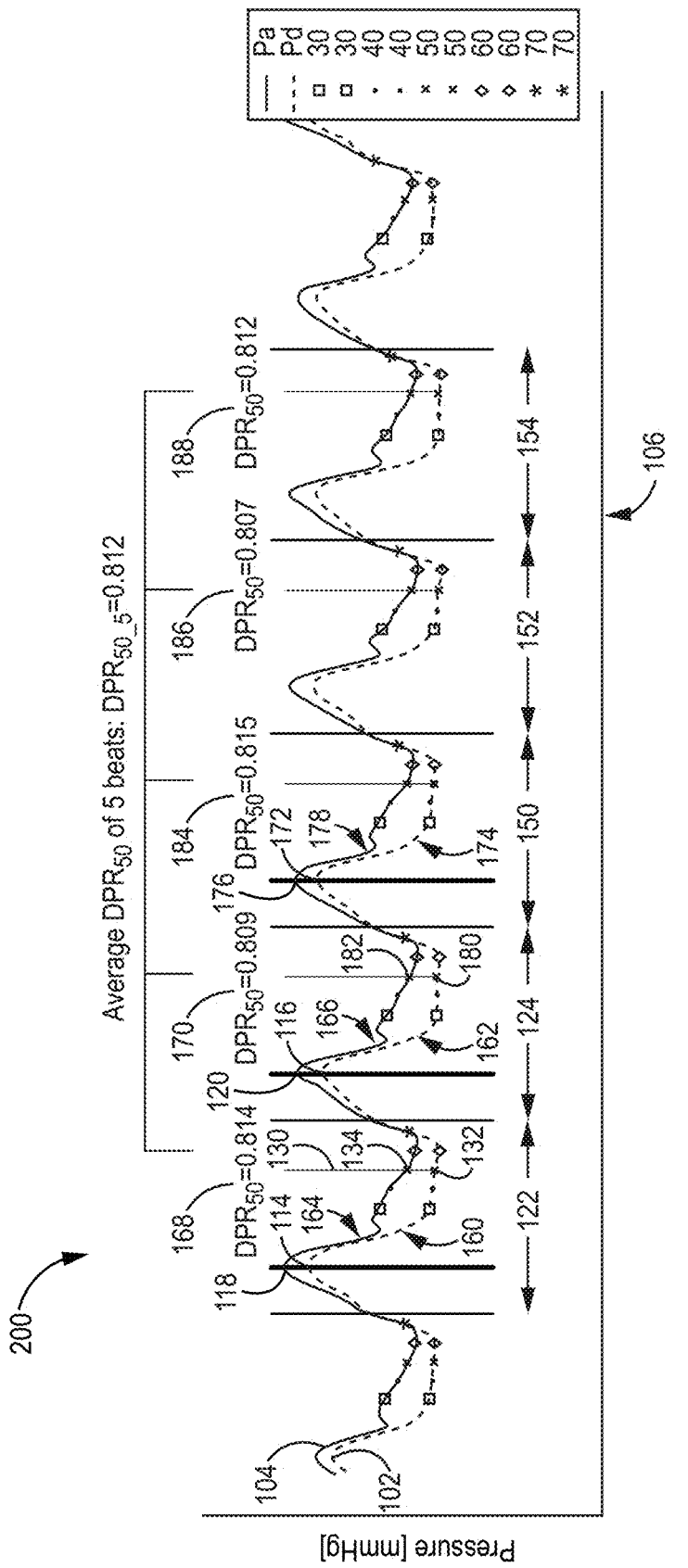
FIG. 4 is a graphical representation of pressure measurements taken over a number of cycles and that can be used to calculate a numerical value, such as a pressure ratio, according to another exemplary embodiment.

FIG. 4 shows a graphical representation 200 of pressure measurements taken over a number of predefined time intervals of the first time period 106. According to one exemplary embodiment described herein with reference to FIG. 4, a pressure ratio can be calculated using pressure measurements from each of two or more of different predefined time intervals. This may be useful in providing a larger sample size from which to calculate the pressure ratio and thereby may act to increase accuracy.

Referring to the example shown in FIG. 4, the first time period 106 includes a number of predefined time intervals. As shown here, the first time period 106 includes the first predefined time interval 122 and the second predefined time interval 124 subsequent in time to the first predefined time intervals 122. The set of first location pressure measurements 102 form a first location pressure waveform that includes a first cycle 160 of first location pressure measurements over the first predefined time interval 122 and a second cycle 162 of first location pressure measurements over the second predefined time interval 124. Similarly, the set of second location pressure measurements 104 form a second location pressure waveform that includes a first cycle 164 of second location pressure measurements over the first predefined time interval 122 and a second cycle 166 of second location pressure measurements over the second predefined time interval 124. In an exemplary application described here, the first cycle 160 of first location pressure measurements and the first cycle 164 of second location pressure measurements can each correspond to a first cardiac cycle to which the first predefined time interval 122 is set. Also, in this same exemplary application described here, the second cycle 162 of first location pressure measurements and the second cycle 166 of second location pressure measurements can each correspond to a second cardiac cycle to which the second predefined time interval 124 is set.

By obtaining pressure measurements over a number of different predefined time intervals set to correspond to respective different cycles, a pressure ratio can be calculated using pressure measurements from different cycles. For example, a first predefined time interval pressure ratio 168 can be calculated using an average of one or more pressure measurements from the first cycle 160 of first location pressure measurements and one or more pressure measurements from the first cycle 164 of second location pressure measurements. In addition, a second predefined time interval pressure ratio 170 can be calculated using an average of one or more pressure measurements from the second cycle 162 of first location pressure measurements and one or more pressure measurements from the second cycle 166 of second location pressure measurements. Then, this first predefined time interval pressure ratio 168 and this second predefined time interval pressure ratio 170 can be averaged to provide a pressure ratio calculated using pressure measurements from different cycles.

More specifically, as detailed previously, the one or more pressure measurements used from each of the cycles 160, 162, 164, 166 can be selected relative to identified leading and trailing characteristics.

The first leading characteristic 114 and the first trailing characteristic 116 can be identified and the one or more pressure measurements from the first cycle 160 of first location pressure measurements can be selected between the identified first leading characteristic 114 and first trailing characteristic 116. Also, the second leading characteristic 118 and the second trailing characteristic 120 can be identified and the one or more pressure measurements from the first cycle 164 of second location pressure measurements can be selected between the identified second leading characteristic 118 and second trailing characteristic 120. As shown in FIG. 4, the first predefined time interval pressure ratio 168 is calculated using i) the pressure measurement 132 from the first cycle 160 of first location pressure measurements that is midway between the identified first leading characteristic 114 and first trailing characteristic 116 (or at fifty percent of the time spanning between the time associated with the leading characteristic 114 and the time associated with the trailing characteristic 116) and ii) the pressure measurement 134 from the first cycle 164 of second location pressure measurements that is midway between the identified second leading characteristic 118 and second trailing characteristic 120 (or at fifty percent of the time spanning between the time associated with the leading characteristic 118 and the time associated with the trailing characteristic 120). As described previously, pressure measurements at one or more other particular locations between the respective leading characteristic 114, 118 and respective trailing characteristic 116, 120 can be used. Examples of such pressure measurements at one or more other particular locations between the respective leading characteristic 114, 118 and respective trailing characteristic 116, 120 are shown in FIG. 4 along each respective waveform using visually unique markers, each of which is detailed by the key at the right-hand side of FIG. 4.

To select the one or more pressure measurements from the second cycle 162 of first location pressure measurements and the one or more pressure measurements from the second cycle 166 of second location pressure measurements, respective leading and trailing characteristics can again be identified. For example, a third leading characteristic associated with one or more pressure measurements in the second cycle 162 of first location pressure measurements can be identified and a fourth leading characteristic associated with one or more pressure measurements in the second cycle 166 of second location pressure measurements can be identified. In the example shown in FIG. 4, the first trailing characteristic 116 serves as the third leading characteristic and the second trailing characteristic 120 serves as the fourth leading characteristic. In addition, a third trailing characteristic 172 associated with one or more pressure measurements in a third cycle 174 of first location pressure measurements over a third predefined time interval 150 of the first time period 106 can be identified. And, a fourth trailing characteristic 176 associated with one or more pressure measurements in a third cycle 178 of second location pressure measurements over the third predefined time interval 150 can be identified. In this example, the third trailing characteristic 172 and the fourth trailing characteristic 176 can each be a maximum pressure measurement in the respective sets of first and second location pressure measurements 102, 104 over the third predefined time period 150. The identified third trailing characteristic 172 can be after the identified third leading characteristic in the set of first location pressure measurements 102 and the identified fourth trailing characteristic 176 can be after the identified fourth leading characteristic in the set of second location pressure measurements 104.

One or more pressure measurements from the second cycle 162 of first location pressure measurements can be selected between the identified third leading characteristic and the identified third trailing characteristic 172. Also, one or more pressure measurements from the second cycle 166 of second location pressure measurements can be selected between the identified fourth leading characteristic and the identified fourth trailing characteristic 176. As shown in FIG. 4, the second predefined time interval pressure ratio 170 is calculated using i) a pressure measurement 180 from the second cycle 162 of first location pressure measurements that is midway between the identified third leading characteristic and third trailing characteristic 172 (or at fifty percent of the time spanning between the time associated with the third leading characteristic and the time associated with the third trailing characteristic 172) and ii) a pressure measurement 182 from the second cycle 166 of second location pressure measurements that is midway between the identified fourth leading characteristic and fourth trailing characteristic 176 (or at fifty percent of the time spanning between the time associated with the fourth leading characteristic and the time associated with the fourth trailing characteristic 176). As described previously, pressure measurements at one or more other particular locations between the respective third and fourth leading characteristics and respective third and fourth trailing characteristics 172, 176 can be used. Examples of such pressure measurements at one or more other particular locations between the respective third and fourth leading characteristics and respective third and fourth trailing characteristics 172, 176 are shown in FIG. 4 along each respective waveform using visually unique markers, each of which is detailed by the key at the right-hand side of FIG. 4.

Having calculated the first predefined time interval pressure ratio 168 and the second predefined time interval pressure ratio 170, a pressure ratio across two different cycles, corresponding to the time periods 122 and 124, can be calculated by averaging the first predefined time interval pressure ratio 168 and the second predefined time interval pressure ratio 170.

In some embodiments, as shown in FIG. 4, a pressure ratio can be calculated across more than two different cycles. FIG. 4 additionally shows a fourth predefined time interval 152 and a fifth predefined time interval 154. In the same manner described immediately above, leading and trailing characteristics can be identified to select one or more pressure measurements located therebetween which in turn can be used to calculate a pressure ration for additional cycles so as to increase the sample size for providing an approximation of FFR. As shown here, in addition to calculating the first predefined time interval pressure ratio 168 and the second predefined time interval pressure ratio 170, a third predefined time interval pressure ratio 184, a fourth predefined time interval pressure ratio 186, and a fifth predefined time interval pressure ration 188 can also be calculated. Each of the predefined time interval pressure ratios 168, 170, 184, 186, and 188 can be averaged to provide a pressure ratio calculated using pressure measurements from five different cycles as shown in FIG. 4.

It is noted that, as illustrated by the example of FIG. 4, an identified leading characteristic may be associated with one or more pressure measurements occurring in a different cycle of pressure measurements than those one or more pressure measurements associated with an identified trailing characteristic. For instance, as illustrated here, the identified first leading characteristic 114 may be associated with one or more pressure measurements in the first cycle 160 of first location pressure measurements while the identified first trailing characteristic 116 may be associated with one or more pressure measurements in the second cycle 162 of first location pressure measurements. Likewise, the identified second leading characteristic 118 may be associated with one or more pressure measurements in the first cycle 164 of second location pressure measurements while the identified second trailing characteristic 120 may be associated with one or more pressure measurements in the second cycle 166 of second location pressure measurements.

The exemplary embodiments disclosed up to this point have been described and illustrated using a maximum pressure measurement as one example of an identified characteristic type. Further exemplary embodiments will be described as follows where other examples of identifiable characteristic types can be utilized.

FIG. 5 again shows the graphical representation 100 of pressure measurements that can be used to calculate a pressure ratio. The details provided previously herein are to apply equally to the embodiment described with respect to FIG. 5 except as otherwise noted. In particular, FIG. 5 illustrates a further exemplary embodiment of a technique for calculating a pressure ratio to approximate FFR where a minimum pressure measurement characteristic type is identified and used to select pressure measurements relative thereto for use in calculating the pressure ratio to approximate FFR.

Figure 5:
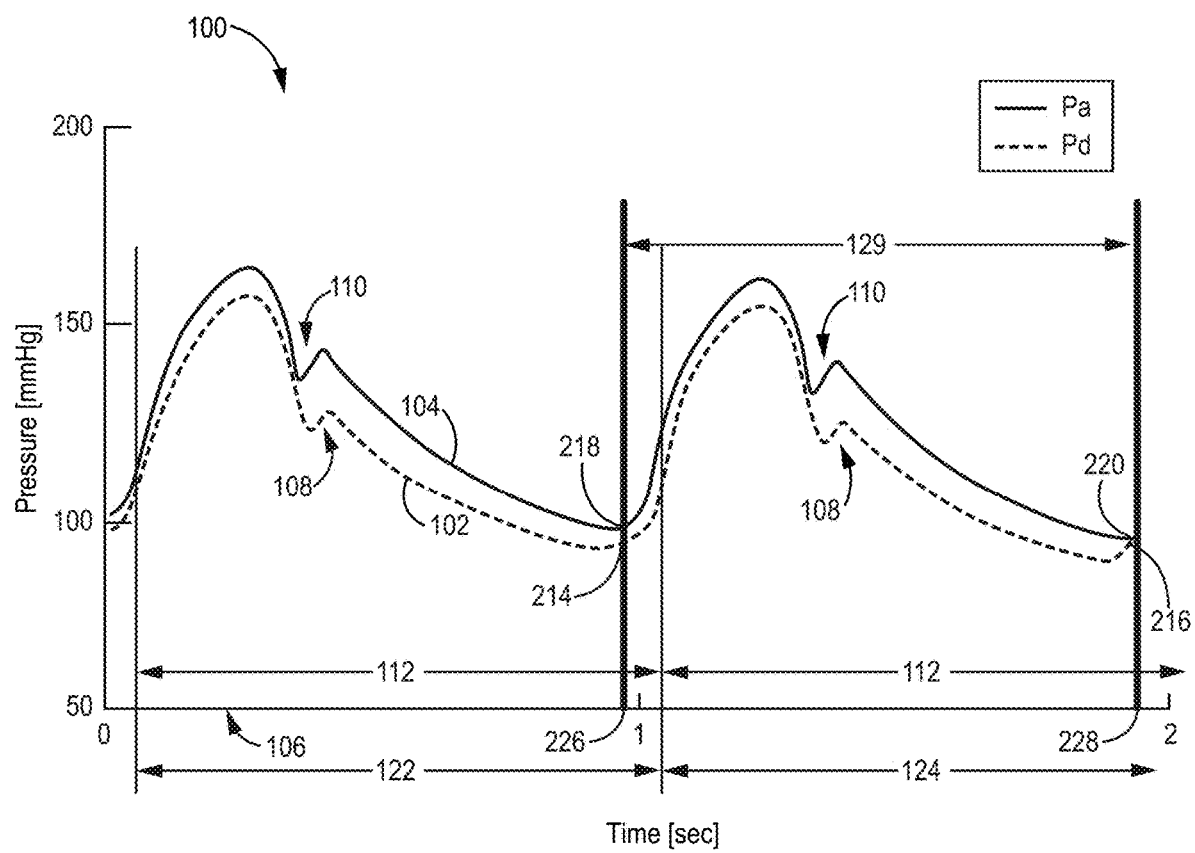
FIG. 5 is a graphical representation of pressure measurements that can be used to calculate a numerical value, such as a pressure ratio, according to a further exemplary embodiment. In particular.

FIG. 5 shows the graphical representation 100 of the set of first location pressure measurements 102 and the set of second location pressure measurements 104 taken over the first time period 106 as described previously. As again shown here, the set of first location pressure measurements 102 includes the dicrotic notch 108 and the set of second location pressure measurements 104 includes the dicrotic notch 110, where the dicrotic notches 108, 110 represent closure of the aortic valve at the onset of ventricular diastole during the cardiac cycle 112.

For the set of first location pressure measurements 102, a first leading characteristic 214 and a first trailing characteristic 216 are identified. The identified first trailing characteristic 216 is after the identified first leading characteristic 214 in the first time period 106. The first leading characteristic 214 is associated with one or more pressure measurements in the set of first location pressure measurements 102 and the first trailing characteristic 216 is associated with one or more pressure measurements in the set of first location pressure measurements 102. The one or more pressure measurements in the set of first location pressure measurements 102 with which the first trailing characteristic 216 is associated can be different (e.g., taken at a different time) than the one or more pressure measurements in the set of first location pressure measurements 102 with which the first leading characteristic 214 is associated.

As noted, in the exemplary embodiment described in reference to FIG. 5, a minimum pressure measurement is the type of characteristic to be identified and used to select pressure measurements relative thereto for use in calculating a pressure ratio approximating FFR. In particular, here the first leading characteristic 214 and the first trailing characteristic 216 are characteristics identified as a minimum pressure measurement in the set of first location pressure measurements 102. In the example shown here, the first leading characteristic 214 is identified as a minimum pressure measurement in the set of first location pressure measurements 102 within the first predefined time interval 122 of the first time period 106. Also in the example shown here, the first trailing characteristic 216 is identified as a minimum pressure measurement in the set of first location pressure measurements 102 within the second predefined time interval 124 of the first time period 106 that is subsequent to the first predefined time interval 122.

The first leading characteristic 214 and the first trailing characteristic 216 are not associated with pressure measurements representing the dicrotic notch 108. Instead, each of the first leading characteristic 214 and the first trailing characteristic 216 is associated with one or more pressure measurements in the set of first location pressure measurements 102 that is obtained at a time (e.g., a time 226, a time 228) in the first time period 106 that differs from a time in the first time period 106 at which the dicrotic notch 108 is present in the set of first location pressure measurements 102.

For the set of second location pressure measurements 104, a second leading characteristic 218 and a second trailing characteristic 220 are identified. The identified second trailing characteristic 220 is after the identified second leading characteristic 218 in the first time period 106. The second leading characteristic 218 is associated with one or more pressure measurements in the set of second location pressure measurements 104 and the second trailing characteristic 220 is associated with one or more pressure measurements in the set of second location pressure measurements 104. The one or more pressure measurements in the set of second location pressure measurements 104 with which the second trailing characteristic 220 is associated can be different (e.g., taken at a different time) than the one or more pressure measurements in the set of second location pressure measurements 104 with which the second leading characteristic 218 is associated.

As noted, in the embodiment of the technique described in reference to FIG. 5, the second leading characteristic 218 and the second trailing characteristic 220 are characteristics identified as a minimum pressure measurement in the set of second location pressure measurements 104. In the example shown here, the second leading characteristic 218 can be identified as a minimum pressure measurement in the set of second location pressure measurements 104 within the first predefined time interval 122. Also in the example shown here, the second trailing characteristic 220 can be identified as a minimum pressure measurement in the set of second location pressure measurements 104 within the second predefined time interval 124. In some cases, an identified minimum pressure measurement may represent more than one individual pressure measurement in the set of first location pressure measurements 102 and/or the set of second location pressure measurements 104. For example, in either or both of these sets an identified minimum pressure measurement can be identified as corresponding to an average time in the respective predefined time interval that represents multiple consecutive localized minimum pressure measurements as is shown for the first leading characteristic 214. This can be useful, for instance, in aligning identified leading and/or trailing characteristics from the different sets 102, 104 at a common time in the respective predefined time interval.

The second leading characteristic 218 and the second trailing characteristic 220 are not associated with pressure measurements representing the dicrotic notch 110. Instead, each of the second leading characteristic 218 and the second trailing characteristic 220 is associated with one or more pressure measurements in the set of second location pressure measurements 104 that is obtained at a time (e.g., a time 226, a time 228) in the first time period 106 that differs from a time in the first time period 106 at which the dicrotic notch 110 is present in the set of second location pressure measurements 104.

In some cases, as shown in FIG. 5, the minimum pressure measurement identified as the first leading characteristic 214 and the minimum pressure measurement identified as the second leading characteristic 218 may be at a same time 226 in the first time period 106. Similarly, in some cases, as shown in FIG. 5, the minimum pressure measurement identified as the first trailing characteristic 216 and the minimum pressure measurement identified as the second trailing characteristic 220 may be at a same time 228 in the first time period 106.

These identified leading and trailing characteristics can serve as references for selecting pressure measurements that are used to calculate a pressure ratio. For instance, a pressure measurement can be selected in the set of first location pressure measurements 102 between the identified first leading characteristic 214 and the identified first trailing characteristic 216. Likewise, a pressure measurement can be selected in the set of second location pressure measurements 104 between the identified second leading characteristic 218 and the identified second trailing characteristic 220. In one case, the selected pressure measurement between the identified first leading characteristic 214 and the identified first trailing characteristic 216 and the selected pressure measurement between the second leading characteristic 218 and the identified second trailing characteristic 220 can be obtained at the same time in the first time period 106. Then, a pressure ratio can be calculated using i) the selected pressure measurement between the identified first leading characteristic 214 and the identified first trailing characteristic 216 and ii) the selected pressure measurement between the second leading characteristic 218 and the identified second trailing characteristic 220. In other instances, pressure measurements can be selected relative to the identified leading and trailing characteristics at locations other than between the identified leading and trailing characteristics.

For example, in the same way as described with reference to FIG. 3, two or more pressure measurements from each set between the respective identified minimum pressure measurement characteristics 214, 216 and 218, 220 in FIG. 5 can be used in calculating the pressure ratio. This includes, as described with reference to FIG. 3, selecting each of these two or more pressure measurements at one or more particular locations between the respective leading and trailing characteristics and, in some cases, combining these pressure measurements from the one or more particular locations, and using the combined pressure measurements to then calculate a pressure ratio.

Also, in the same way as described with reference to FIG. 4, a pressure ratio can be calculated using identified minimum pressure measurement characteristics associated with two or more of different predefined time intervals over the first time period 106 to select pressure measurements from each of two or more of the different predefined time intervals over the first time period 106.

Figure 6:
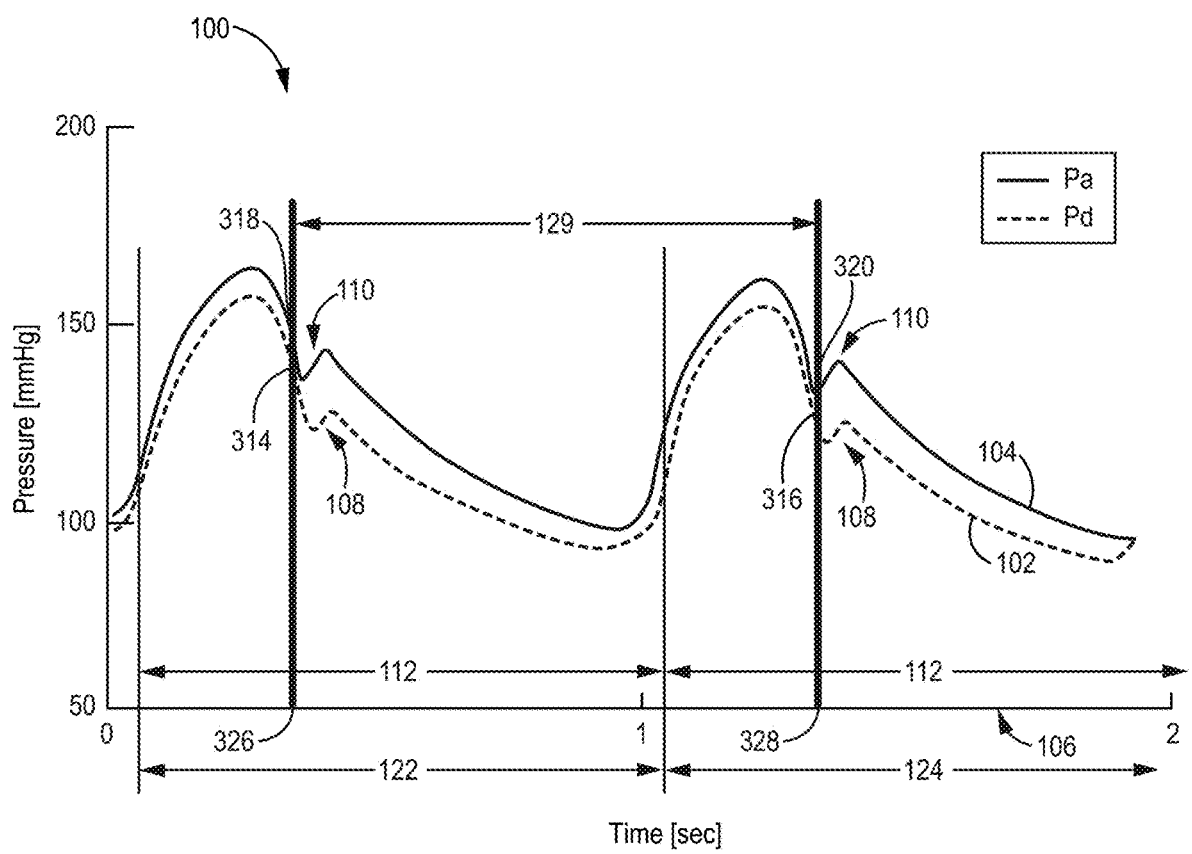
FIG. 6 is a graphical representation of pressure measurements that can be used to calculate a numerical value, such as a pressure ratio, according to an additional exemplary embodiment. In particular.

FIG. 6 again shows the graphical representation 100 of pressure measurements that can be used to calculate a pressure ratio. The details provided previously herein are to apply equally to the embodiment described with respect to FIG. 6 except as otherwise noted. In particular, FIG. 6 illustrates a further exemplary embodiment of a technique for calculating a pressure ratio to approximate FFR where a maximum decreasing pressure measurement rate of change characteristic type is identified and used to select pressure measurements relative thereto for use in calculating the pressure ratio to approximate FFR. A maximum decreasing pressure measurement rate of change may be identified, for instance, when a difference between consecutive pressure measurements constitutes a decrease in pressure that is a greater decrease in pressure than that between other consecutive pressure measurements taken at different times. In the context of the pressure waveforms shown in FIG. 6, the maximum decreasing pressure measurement rate of change can be represented by a maximum descending slope in the waveform for the respective set of pressure measurements 102, 104. As detailed below, the maximum decreasing pressure measurement rate of change characteristic can be identified within a predefined time interval of the first time period 106.

FIG. 6 shows the graphical representation 100 of the set of first location pressure measurements 102 and the set of second location pressure measurements 104 taken over the first time period 106 as described previously. As again shown here, the set of first location pressure measurements 102 includes the dicrotic notch 108 and the set of second location pressure measurements 104 includes the dicrotic notch 110, where the dicrotic notches 108, 110 represent closure of the aortic valve at the onset of ventricular diastole during the cardiac cycle 112.

For the set of first location pressure measurements 102, a first leading characteristic 314 and a first trailing characteristic 316 are identified. The identified first trailing characteristic 316 is after the identified first leading characteristic 314 in the first time period 106. The first leading characteristic 314 is associated with one or more pressure measurements in the set of first location pressure measurements 102 and the first trailing characteristic 316 is associated with one or more pressure measurements in the set of first location pressure measurements 102. The one or more pressure measurements in the set of first location pressure measurements 102 with which the first trailing characteristic 316 is associated can be different (e.g., taken at a different time) than the one or more pressure measurements in the set of first location pressure measurements 102 with which the first leading characteristic 314 is associated.

As noted, in the exemplary embodiment described in reference to FIG. 6, a maximum decreasing pressure measurement rate of change is the type of characteristic to be identified and used to select pressure measurements relative thereto for use in calculating a pressure ratio approximating FFR. In particular, here the first leading characteristic 314 and the first trailing characteristic 316 are characteristics identified as a maximum decreasing pressure measurement rate of change in the set of first location pressure measurements 102. In the example shown here, the first leading characteristic 314 is identified as a maximum decreasing pressure measurement rate of change in the set of first location pressure measurements 102 within the first predefined time interval 122 of the first time period 106. Also in the example shown here, the first trailing characteristic 316 is identified as a maximum decreasing pressure measurement rate of change in the set of first location pressure measurements 102 within the second predefined time interval 124 of the first time period 106 that is subsequent to the first predefined time interval 122.

The first leading characteristic 314 and the first trailing characteristic 316 are not associated with pressure measurements representing the dicrotic notch 108. Instead, each of the first leading characteristic 314 and the first trailing characteristic 316 is associated with one or more pressure measurements in the set of first location pressure measurements 102 that is obtained at a time (e.g., a time 326, a time 328) in the first time period 106 that differs from a time in the first time period 106 at which the dicrotic notch 108 is present in the set of first location pressure measurements 102.

For the set of second location pressure measurements 104, a second leading characteristic 318 and a second trailing characteristic 320 are identified. The identified second trailing characteristic 320 is after the identified second leading characteristic 318 in the first time period 106. The second leading characteristic 318 is associated with one or more pressure measurements in the set of second location pressure measurements 104 and the second trailing characteristic 320 is associated with one or more pressure measurements in the set of second location pressure measurements 104. The one or more pressure measurements in the set of second location pressure measurements 104 with which the second trailing characteristic 320 is associated can be different (e.g., taken at a different time) than the one or more pressure measurements in the set of second location pressure measurements 104 with which the second leading characteristic 318 is associated.

As noted, in the embodiment of the technique described in reference to FIG. 6, the second leading characteristic 318 and the second trailing characteristic 320 are characteristics identified as a maximum decreasing pressure measurement rate of change in the set of second location pressure measurements 104. In the example shown here, the second leading characteristic 318 can be identified as a maximum decreasing pressure measurement rate of change in the set of second location pressure measurements 104 within the first predefined time interval 122. Also in the example shown here, the second trailing characteristic 320 can be identified as a maximum decreasing pressure measurement rate of change in the set of second location pressure measurements 104 within the second predefined time interval 124. In some cases, an identified maximum decreasing pressure measurement rate of change may represent more than one individual pressure measurement in the set of first location pressure measurements 102 and/or the set of second location pressure measurements 104. For example, in either or both of these sets an identified maximum decreasing pressure measurement rate of change can be identified as corresponding to a time in the respective predefined time interval that represents an average time of multiple localized pressure measurements having a same, or substantially similar, decreasing rate of change therebetween. This can be useful, for instance, in aligning identified leading and/or trailing characteristics from the different sets 102, 104 at a common time in the respective predefined time interval.

The second leading characteristic 318 and the second trailing characteristic 320 are not associated with pressure measurements representing the dicrotic notch 110. Instead, each of the second leading characteristic 318 and the second trailing characteristic 320 is associated with one or more pressure measurements in the set of second location pressure measurements 104 that is obtained at a time (e.g., a time 326, a time 328) in the first time period 106 that differs from a time in the first time period 106 at which the dicrotic notch 110 is present in the set of second location pressure measurements 104.

In some cases, as shown in FIG. 6, the maximum decreasing pressure measurement rate of change identified as the first leading characteristic 314 and the maximum decreasing pressure measurement rate of change identified as the second leading characteristic 318 may be at a same time 326 in the first time period 106 Similarly, in some cases, as shown in FIG. 6, the maximum decreasing pressure measurement rate of change identified as the first trailing characteristic 316 and the maximum decreasing pressure measurement rate of change identified as the second trailing characteristic 320 may be at a same time 328 in the first time period 106.

These identified leading and trailing characteristics can serve as references for selecting pressure measurements that are used to calculate a pressure ratio. For instance, a pressure measurement can be selected in the set of first location pressure measurements 102 between the identified first leading characteristic 314 and the identified first trailing characteristic 316. Likewise, a pressure measurement can be selected in the set of second location pressure measurements 104 between the identified second leading characteristic 318 and the identified second trailing characteristic 320. In one case, the selected pressure measurement between the identified first leading characteristic 314 and the identified first trailing characteristic 316 and the selected pressure measurement between the second leading characteristic 318 and the identified second trailing characteristic 320 can be obtained at the same time in the first time period 106. Then, a pressure ratio can be calculated using i) the selected pressure measurement between the identified first leading characteristic 314 and the identified first trailing characteristic 316 and ii) the selected pressure measurement between the second leading characteristic 318 and the identified second trailing characteristic 320. In other instances, pressure measurements can be selected relative to the identified leading and trailing characteristics at locations other than between the identified leading and trailing characteristics.

For example, in the same way as described with reference to FIG. 3, two or more pressure measurements from each set between the respective identified maximum decreasing pressure measurement rate of change characteristics 314, 316 and 318, 320 in FIG. 6 can be used in calculating the pressure ratio. This includes, as described with reference to FIG. 3, selecting each of these two or more pressure measurements at one or more particular locations between the respective leading and trailing characteristics and, in some cases, combining these pressure measurements from the one or more particular locations, and using the combined pressure measurements to then calculate a pressure ratio.

Also, in the same way as described with reference to FIG. 4, a pressure ratio can be calculated using identified maximum decreasing pressure measurement rate of change characteristics associated with two or more of different predefined time intervals over the first time period 106 to select pressure measurements from each of two or more of the different predefined time intervals over the first time period 106.

Figure 7:
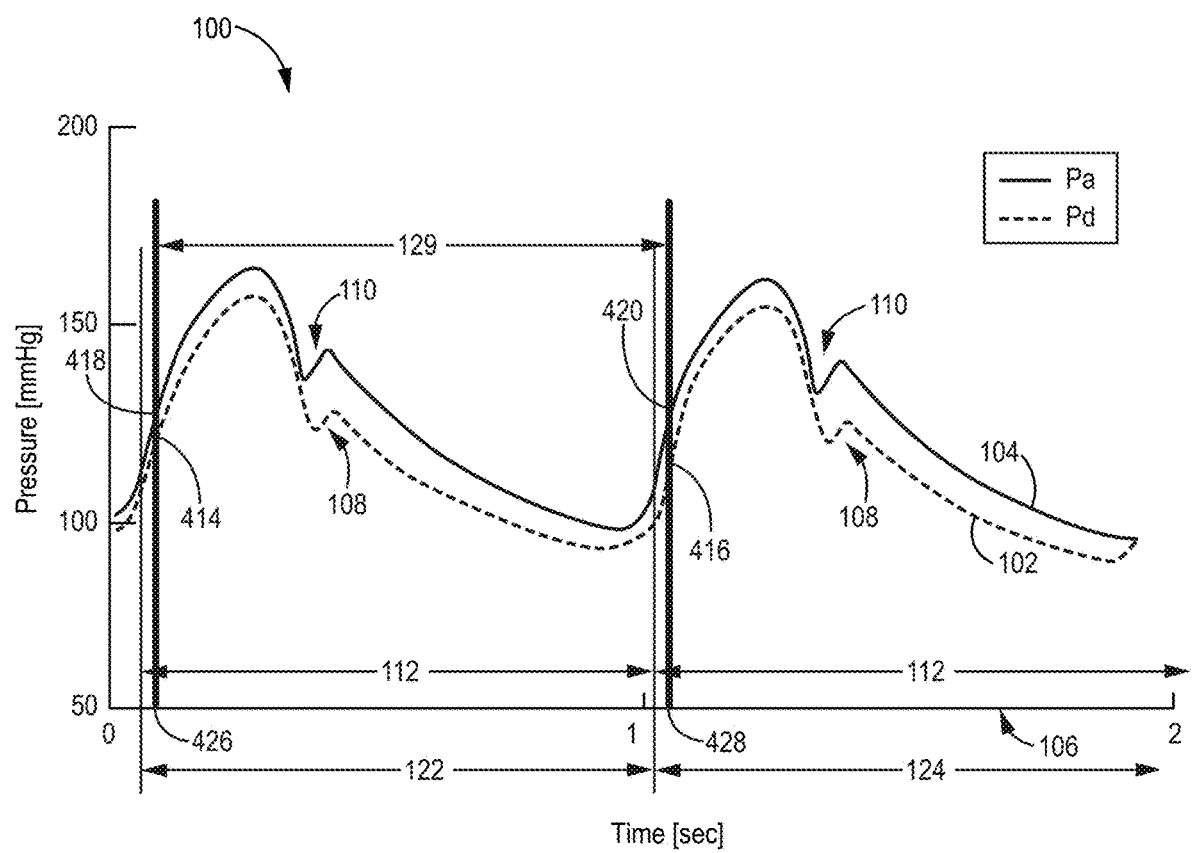
FIG. 7 is a graphical representation of pressure measurements that can be used to calculate a numerical value, such as a pressure ratio, according to another exemplary embodiment. In particular.

FIG. 7 again shows the graphical representation 100 of pressure measurements that can be used to calculate a pressure ratio. The details provided previously herein are to apply equally to the embodiment described with respect to FIG. 7 except as otherwise noted. In particular, FIG. 7 illustrates a further exemplary embodiment of a technique for calculating a pressure ratio to approximate FFR where a maximum increasing pressure measurement rate of change characteristic type is identified and used to select pressure measurements relative thereto for use in calculating the pressure ratio to approximate FFR. A maximum increasing pressure measurement rate of change may be identified, for instance, when a difference between consecutive pressure measurements constitutes an increase in pressure that is a greater increase in pressure than that between other consecutive pressure measurements taken at different times. In the context of the pressure waveforms shown in FIG. 7, the maximum increasing pressure measurement rate of change can be represented by a maximum ascending slope in the waveform for the respective set of pressure measurements 102, 104. As detailed below, the maximum increasing pressure measurement rate of change characteristic can be identified within a predefined time interval of the first time period 106.

FIG. 7 shows the graphical representation 100 of the set of first location pressure measurements 102 and the set of second location pressure measurements 104 taken over the first time period 106 as described previously. As again shown here, the set of first location pressure measurements 102 includes the dicrotic notch 108 and the set of second location pressure measurements 104 includes the dicrotic notch 110, where the dicrotic notches 108, 110 represent closure of the aortic valve at the onset of ventricular diastole during the cardiac cycle 112.

For the set of first location pressure measurements 102, a first leading characteristic 414 and a first trailing characteristic 416 are identified. The identified first trailing characteristic 416 is after the identified first leading characteristic 414 in the first time period 106. The first leading characteristic 414 is associated with one or more pressure measurements in the set of first location pressure measurements 102 and the first trailing characteristic 416 is associated with one or more pressure measurements in the set of first location pressure measurements 102. The one or more pressure measurements in the set of first location pressure measurements 102 with which the first trailing characteristic 416 is associated can be different (e.g., taken at a different time) than the one or more pressure measurements in the set of first location pressure measurements 102 with which the first leading characteristic 414 is associated.

As noted, in the exemplary embodiment described in reference to FIG. 7, a maximum increasing pressure measurement rate of change is the type of characteristic to be identified and used to select pressure measurements relative thereto for use in calculating a pressure ratio approximating FFR. In particular, here the first leading characteristic 414 and the first trailing characteristic 416 are characteristics identified as a maximum increasing pressure measurement rate of change in the set of first location pressure measurements 102. In the example shown here, the first leading characteristic 414 is identified as a maximum increasing pressure measurement rate of change in the set of first location pressure measurements 102 within the first predefined time interval 122 of the first time period 106. Also in the example shown here, the first trailing characteristic 416 is identified as a maximum increasing pressure measurement rate of change in the set of first location pressure measurements 102 within the second predefined time interval 124 of the first time period 106 that is subsequent to the first predefined time interval 122.

The first leading characteristic 414 and the first trailing characteristic 416 are not associated with pressure measurements representing the dicrotic notch 108. Instead, each of the first leading characteristic 414 and the first trailing characteristic 416 is associated with one or more pressure measurements in the set of first location pressure measurements 102 that is obtained at a time (e.g., a time 426, a time 428) in the first time period 106 that differs from a time in the first time period 106 at which the dicrotic notch 108 is present in the set of first location pressure measurements 102.

For the set of second location pressure measurements 104, a second leading characteristic 418 and a second trailing characteristic 420 are identified. The identified second trailing characteristic 420 is after the identified second leading characteristic 418 in the first time period 106. The second leading characteristic 418 is associated with one or more pressure measurements in the set of second location pressure measurements 104 and the second trailing characteristic 420 is associated with one or more pressure measurements in the set of second location pressure measurements 104. The one or more pressure measurements in the set of second location pressure measurements 104 with which the second trailing characteristic 420 is associated can be different (e.g., taken at a different time) than the one or more pressure measurements in the set of second location pressure measurements 104 with which the second leading characteristic 418 is associated.

As noted, in the embodiment of the technique described in reference to FIG. 7, the second leading characteristic 418 and the second trailing characteristic 420 are characteristics identified as a maximum increasing pressure measurement rate of change in the set of second location pressure measurements 104. In the example shown here, the second leading characteristic 418 can be identified as a maximum increasing pressure measurement rate of change in the set of second location pressure measurements 104 within the first predefined time interval 122. Also in the example shown here, the second trailing characteristic 420 can be identified as a maximum increasing pressure measurement rate of change in the set of second location pressure measurements 104 within the second predefined time interval 124. In some cases, an identified maximum increasing pressure measurement rate of change may represent more than one individual pressure measurement in the set of first location pressure measurements 102 and/or the set of second location pressure measurements 104. For example, in either or both of these sets an identified maximum increasing pressure measurement rate of change can be identified as corresponding to a time in the respective predefined time interval that represents an average time of multiple localized pressure measurements having a same, or substantially similar, increasing rate of change therebetween. This can be useful, for instance, in aligning identified leading and/or trailing characteristics from the different sets 102, 104 at a common time in the respective predefined time interval.

The second leading characteristic 418 and the second trailing characteristic 420 are not associated with pressure measurements representing the dicrotic notch 110. Instead, each of the second leading characteristic 418 and the second trailing characteristic 420 is associated with one or more pressure measurements in the set of second location pressure measurements 104 that is obtained at a time (e.g., a time 426, a time 428) in the first time period 106 that differs from a time in the first time period 106 at which the dicrotic notch 110 is present in the set of second location pressure measurements 104.

In some cases, as shown in FIG. 7, the maximum increasing pressure measurement rate of change identified as the first leading characteristic 414 and the maximum increasing pressure measurement rate of change identified as the second leading characteristic 418 may be at a same time 426 in the first time period 106 Similarly, in some cases, as shown in FIG. 7, the maximum increasing pressure measurement rate of change identified as the first trailing characteristic 416 and the maximum increasing pressure measurement rate of change identified as the second trailing characteristic 420 may be at a same time 428 in the first time period 106.

These identified leading and trailing characteristics can serve as references for selecting pressure measurements that are used to calculate a pressure ratio. For instance, a pressure measurement can be selected in the set of first location pressure measurements 102 between the identified first leading characteristic 414 and the identified first trailing characteristic 416. Likewise, a pressure measurement can be selected in the set of second location pressure measurements 104 between the identified second leading characteristic 418 and the identified second trailing characteristic 420. In one case, the selected pressure measurement between the identified first leading characteristic 414 and the identified first trailing characteristic 416 and the selected pressure measurement between the second leading characteristic 418 and the identified second trailing characteristic 420 can be obtained at the same time in the first time period 106. Then, a pressure ratio can be calculated using i) the selected pressure measurement between the identified first leading characteristic 414 and the identified first trailing characteristic 416 and ii) the selected pressure measurement between the second leading characteristic 418 and the identified second trailing characteristic 420. In other instances, pressure measurements can be selected relative to the identified leading and trailing characteristics at locations other than between the identified leading and trailing characteristics.

For example, in the same way as described with reference to FIG. 3, two or more pressure measurements from each set between the respective identified maximum increasing pressure measurement rate of change characteristics 414, 416 and 418, 420 in FIG. 7 can be used in calculating the pressure ratio. This includes, as described with reference to FIG. 3, selecting each of these two or more pressure measurements at one or more particular locations between the respective leading and trailing characteristics and, in some cases, combining these pressure measurements from the one or more particular locations, and using the combined pressure measurements to then calculate a pressure ratio.

Also, in the same way as described with reference to FIG. 4, a pressure ratio can be calculated using identified maximum increasing pressure measurement rate of change characteristics associated with two or more of different predefined time intervals over the first time period 106 to select pressure measurements from each of two or more of the different predefined time intervals over the first time period 106.

Figure 8:
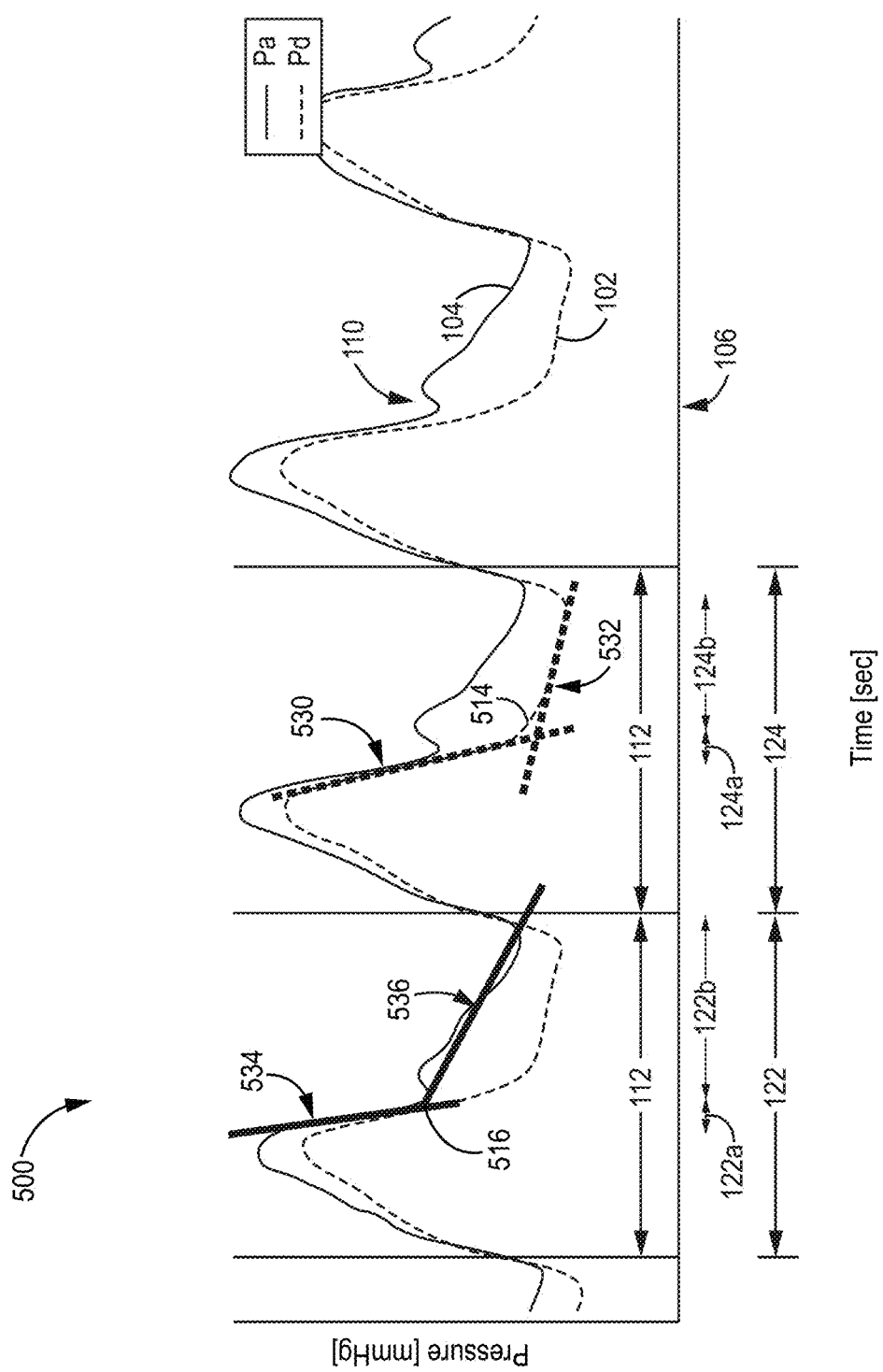
FIG. 8 is a graphical representation of pressure measurements that can be used to calculate a numerical value, such as a pressure ratio, according to a further exemplary embodiment. In particular.

FIG. 8 shows a graphical representation 500 of pressure measurements that can be used to calculate a pressure ratio. The details provided previously herein are to apply equally to the embodiment described with respect to FIG. 8 except as otherwise noted. In particular, FIG. 8 illustrates another exemplary embodiment of a technique for calculating a pressure ratio to approximate FFR where a threshold decreasing pressure measurement rate of change characteristic type is identified and used to select pressure measurements relative thereto for use in calculating the pressure ratio to approximate FFR.

In applications where pressure measurements are taken over cardiac cycles, for example, in each such cycle, for some patients, the pressure measurements may include two different time intervals where pressure measurements over the respective time interval decrease within a threshold rate of change. For instance, as shown in FIG. 8, over the cardiac cycle 112 the set of first location pressure measurements 102 includes a first interval 124a where a group of pressure measurements 530 decrease, from one pressure measurement to a consecutive pressure measurement within the group of pressure measurements 530, within one threshold rate of change. Also over the cardiac cycle 112, the set of first location pressure measurements 102 includes a second interval 124b where a group of pressure measurements 532 decrease, from one pressure measurement to a consecutive pressure measurement within the group of pressure measurements 532, within another threshold rate of change that is different than the one threshold rate of change of the group 530. Likewise, over the cardiac cycle 112, the set of first location pressure measurements 104 includes a first interval 122a where a group of pressure measurements 534 decrease, from one pressure measurement to a consecutive pressure measurement within the group of pressure measurements 534, within one threshold rate of change. And, over the cardiac cycle 112, the set of first location pressure measurements 104 includes a second interval 122b where a group of pressure measurements 536 decrease, from one pressure measurement to a consecutive pressure measurement within the group of pressure measurements 536, within another threshold rate of change that is different than the one threshold rate of change of the group 534.

The threshold rate of change used to ascertain the group of pressure measurements can vary depending on the specific application. For example, a group of pressure measurements can be ascertained as such when pressure measurements over a time interval decrease from one pressure measurement to a consecutive pressure measurement in the time interval by less than 0.5%, 1%, 2%, 3%, 5%, 7.5%, 10%, 15%, 20%, or 25%.

The groups 530 and 532 of the set of first location pressure measurements 102 and the groups 534 and 536 of the set of second location pressure measurements 104 are referenced in FIG. 8 at different cardiac cycles 112 for ease of illustration. Though in many embodiments the groups 530 and 532 of the set of first location pressure measurements 102 and the groups 534 and 536 of the set of second location pressure measurements 104 can be analyzed and used from the same cardiac cycle 112.

A threshold decreasing pressure measurement rate of change may be identified when the pressure measurements in a respective set 102, 104 transition from one group of one threshold rate of change to another group of another, different threshold rate of change. For example, a threshold decreasing pressure measurement rate of change 514 can be identified for the set of first location pressure measurements 102 over a predefined time interval (e.g., the first predefined time interval 122, and/or the second predefined time interval 124 as is shown here) when the pressure measurements transition from the group of pressure measurements 530 to the group of pressure measurements 532. As such, the threshold decreasing pressure measurement rate of change 514 in this example represents a time when the decrease in pressure between a pressure measurement immediately prior in time to the threshold decreasing pressure measurement rate of change 514 and a pressure measurement immediately subsequent in time to the threshold decreasing pressure measurement rate of change 514 is greater than a threshold rate of change Similarly, a threshold decreasing pressure measurement rate of change 516 can be identified for the set of first location pressure measurements 104 over a predefined time interval (e.g., the first predefined time interval 122 as is shown here, and/or the second predefined time interval 124) when the pressure measurements transition from the group of pressure measurements 534 to the group of pressure measurements 536. As such, the threshold decreasing pressure measurement rate of change 516 in this example represents a time when the decrease in pressure between a pressure measurement immediately prior in time to the threshold decreasing pressure measurement rate of change 516 and a pressure measurement immediately subsequent in time to the threshold decreasing pressure measurement rate of change 516 is greater than a threshold rate of change.

The identified threshold decreasing pressure measurement rate of change characteristic can serve as a reference for selecting pressure measurements that are used to calculate a pressure ratio. For instance, a pressure measurement can be selected in the set of first location pressure measurements 102 as being at a particular location (e.g., time) relative to the threshold decreasing pressure measurement rate of change 514. Likewise, a pressure measurement can be selected in the set of second location pressure measurements 104 as being at a particular location (e.g., time) relative to the threshold decreasing pressure measurement rate of change 516. In certain embodiments, a threshold decreasing pressure measurement rate of change characteristic can be identified along with one or more other characteristic types disclosed herein. In such embodiments, a pressure measurement in the set 102 and/or 104 can be selected as being at a particular location relative to the identified threshold decreasing pressure measurement rate of change characteristic and the one or more identified other characteristic types disclosed herein. For instance, one or more pressure measurements taken at a time between an identified threshold decreasing pressure measurement rate of change characteristic and one of an identified maximum pressure measurement, minimum pressure measurement, maximum decreasing pressure measurement rate of change, and maximum increasing pressure measurement rate of change could be selected and used to calculate a pressure ratio.

Identifying a threshold decreasing pressure measurement rate of change may be useful as a reliable means to select appropriate pressure measurements for use in calculating a pressure ration to approximate FFR. For instance, as the graphical representation 500 illustrates, the threshold decreasing pressure measurement rate of change can be identified without reference to the dicrotic notch. This can be useful when a set of pressure measurements does not contain any discernible dicrotic notch, as is the case in FIG. 8 for the set of first location pressure measurements 102.

Figure 9:
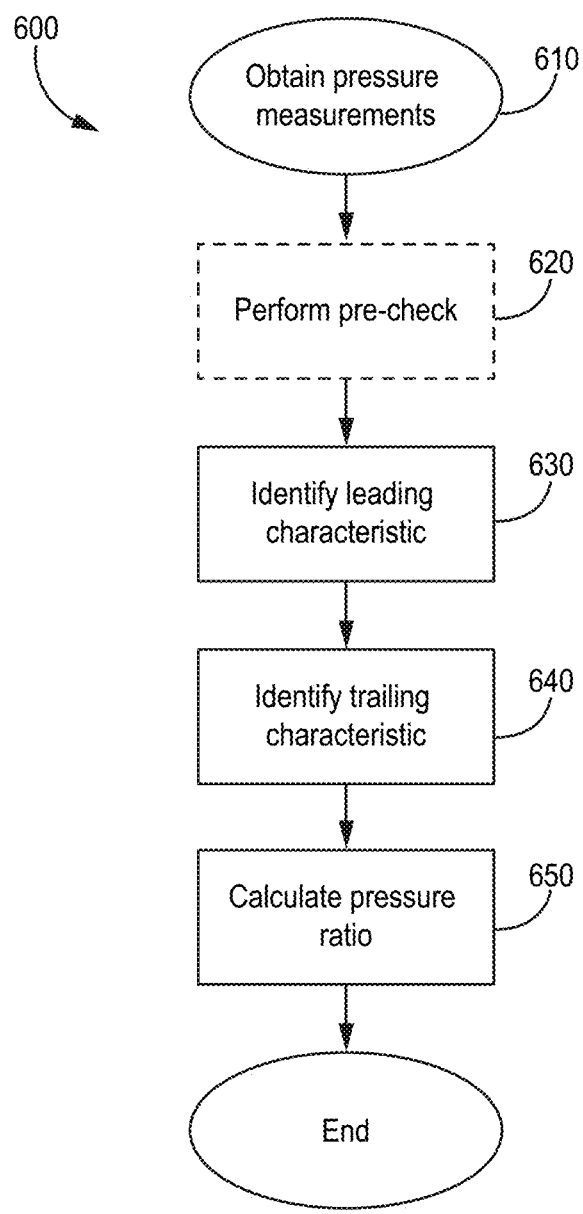
FIG. 9 is a flow diagram of an exemplary embodiment of a method for assessing a vessel, for instance to assess the severity of a restriction at a location of interest in the vessel without administering a hyperemic agent.

FIG. 9 shows a flow diagram of an exemplary embodiment of a method 600 for assessing a vessel. For example, the method described with reference to FIG. 9 could be implemented as actions taken by a user, as an algorithm implemented by computer-executable instructions stored on a non-transitory computer-readable storage article to cause at least one programmable processor to perform the actions, or as a combination that includes both user and algorithm implementation.

At step 610, pressure measurements are obtained. This step can include obtaining a set of first location pressure measurements at a first location in the vessel over a first time period. This step can also include obtaining a set of second location pressure measurements at a second location in the vessel over the first time period. The second location can be different than the first location. In addition, in this step, the set of first location pressure measurements and the set of second location pressure measurements can be obtained not during hyperemia.

In some cases, the method 600 can include step 620. At step 620, a pre-check can be performed. The pre-check can be performed on one or more data points and used to determine whether such data is suitable for use in the method 600. Performing the pre-check can include, for example, determining if the set of first location pressure measurements and the set of second location pressure measurements satisfy a set of pre-check conditions and, if the set of pre-check conditions is satisfied, proceeding to identify leading and trailing characteristics and calculating the pressure ratio.

In one example, the set of pre-check conditions comprises: a minimum pressure measurement in the set of first location (e.g., aortic) pressure measurements is between 30 and 180 mmHg, a maximum pressure measurement in the set of first location pressure measurements is between 40 and 200 mmHg, a minimum pressure measurement in the set of second location (e.g., distal) pressure measurements is between −5 and 180 mmHg, a maximum pressure measurement in the set of second location pressure measurements is between 10 and 200 mmHg, pulse pressure corresponding to the set of first location pressure measurements is at least 10 mmHg, pulse pressure corresponding to the set of second location pressure measurements is at least 5 mmHg, a maximum pressure measurement in the set of second location pressure measurements is less than 108% of a maximum pressure measurement in the set of first location pressure measurements, a minimum pressure measurement in the set of second location pressure measurements is less than 108% of a minimum pressure measurement in the set of first location pressure measurements, heart rate over the first time period (e.g., as averaged across the first time period) is between 40 and 300 beats per minute, and none of the heartbeats over the first time period vary by more than 30% from an average of each other heartbeats occurring during the first time period. Each of these conditions can be evaluated within a time period over which a pressure ratio is to be calculated, for instance over the course of a time period that spans two or more cardiac cycles.

In instances where the method 600 includes performing the pre-check, if one or more pre-check conditions are not satisfied, then the method 600 may include rejecting the pressure measurements obtained at step 610 and performing step 610 again to obtain new pressure measurements. This may be repeated until the pre-check at step 620 is satisfied. As one example, if any one of the above noted pre-check conditions is not met, the method 600 may include rejecting, and thus not using, the pressure measurements obtained at step 610. In this example, once all of the above-noted pre-check conditions are met, the method 600 may proceed on to step 630 and use the pressure measurements obtained in step 610. Thus, determining if the set of first location pressure measurements and the set of second location pressure measurements satisfy the set of pre-check conditions can include determining that each of the conditions comprising the set of pre-check conditions is satisfied. In some instances, the pre-check may be satisfied if fewer than all of the conditions comprising the set of pre-check conditions is satisfied.

At step 630, a leading characteristic is identified. This step can include identifying more than one leading characteristic. For example, this step can include identifying a first leading characteristic associated with one or more pressure measurements in the set of first location pressure measurements and a second leading characteristic associated with one or more pressure measurements in the set of second location pressure measurements. In this step, the identified first leading characteristic and/or the identified second leading characteristic may be a characteristic type selected from the group of characteristic types consisting of: a maximum pressure measurement, a minimum pressure measurement, a maximum decreasing pressure measurement rate of change, and a maximum increasing pressure measurement rate of change. In some further examples, the group of characteristic types from which the identified first leading characteristic and/or the identified second leading characteristic may be selected can also include a threshold decreasing pressure measurement rate of change.

At step 640, a trailing characteristic is identified. This step can include identifying more than one trailing characteristic. For example, this step can include identifying a first trailing characteristic associated with one or more pressure measurements in the set of first location pressure measurements and a second trailing characteristic associated with one or more pressure measurements in the set of second location pressure measurements. In this step, the identified first trailing characteristic and/or the identified second trailing characteristic may be a characteristic type selected from the group of characteristic types consisting of: a maximum pressure measurement, a minimum pressure measurement, a maximum decreasing pressure measurement rate of change, and a maximum increasing pressure measurement rate of change. In some further examples, the group of characteristic types from which the identified first trailing characteristic and/or the identified second trailing characteristic may be selected can also include a threshold decreasing pressure measurement rate of change.

In the method 600, the identified first trailing characteristic can be after the identified first leading characteristic in the first time period and the identified second trailing characteristic can be after the identified second leading characteristic in the first time period. Moreover, at least one of the identified first leading characteristic, the identified second leading characteristic, the identified first trailing characteristic, and the identified second trailing characteristic can be associated with a pressure measurement in the respective set of first location pressure measurements and second location pressure measurements that is obtained at a time in the first time period that differs from a time in the first time period at which a dicrotic notch is present in the respective set of first location pressure measurements and second location pressure measurements.

At step 650, a pressure ratio is calculated. For example, in this step the pressure ratio can be calculated using i) a pressure measurement in the set of first location pressure measurements between the identified first leading characteristic and the identified first trailing characteristic and ii) a pressure measurement in the set of second location pressure measurements between the identified second leading characteristic and the identified second trailing characteristic. In other examples, in this step the pressure ratio can be calculated using a multiple pressure measurements between the respective identified leading and trailing characteristics. For instance, the pressure ratio can be calculated using i) an average of a) one pressure measurement in the set of first location pressure measurements between the identified first leading characteristic and the identified first trailing characteristic and b) another pressure measurement in the set of first location pressure measurements between the identified first leading characteristic and the identified first trailing characteristic, and ii) an average of a) one pressure measurement in the set of second location pressure measurements between the identified second leading characteristic and the identified second trailing characteristic and b) another pressure measurement in the set of second location pressure measurements between the identified second leading characteristic and the identified second trailing characteristic.

Various examples have been described with reference to certain disclosed embodiments. The embodiments are presented for purposes of illustration and not limitation. One skilled in the art will appreciate that various changes, adaptations, and modifications can be made without departing from the scope of the invention.

What is claimed is:

1. A method for assessing a vessel, the method comprising the steps of:
   obtaining a set of first location pressure measurements at a first location in the vessel over a first time period and a set of second location pressure measurements at a second location in the vessel over the first time period, wherein the second location is different than the first location, and wherein the set of first location pressure measurements and the set of second location pressure measurements are obtained not during hyperemia;

identifying a first leading characteristic associated with one or more pressure measurements in the set of first location pressure measurements and a second leading characteristic associated with one or more pressure measurements in the set of second location pressure measurements;

identifying a first trailing characteristic associated with one or more pressure measurements in the set of first location pressure measurements and a second trailing characteristic associated with one or more pressure measurements in the set of second location pressure measurements, wherein the identified first trailing characteristic is after the identified first leading characteristic in the first time period and the identified second trailing characteristic is after the identified second leading characteristic in the first time period, and wherein at least one of the identified first leading characteristic, the identified second leading characteristic, the identified first trailing characteristic, and the identified second trailing characteristic is associated with a pressure measurement in the respective set of first location pressure measurements and second location pressure measurements that is obtained without reference to any dicrotic notch that may be present in the respective set of first location pressure measurements and second location pressure measurements;

calculating a pressure ratio using i) a pressure measurement in the set of first location pressure measurements between the identified first leading characteristic and the identified first trailing characteristic and ii) a pressure measurement in the set of second location pressure measurements between the identified second leading characteristic and the identified second trailing characteristic; and responsive to the pressure ratio exceeding a clinical threshold, performing an interventional procedure.

2. The method of claim 1, wherein the pressure measurement in the set of first location pressure measurements between the identified first leading characteristic and the identified first trailing characteristic and the pressure measurement in the set of second location pressure measurements between the identified second leading characteristic and the identified second trailing characteristic are obtained at the same time in the first time period.

3. The method of claim 2, 
wherein the one or more pressure measurements in the set of first location pressure measurements associated with the identified first leading characteristic and the one or more pressure measurements in the set of second location pressure measurements associated with the identified second leading characteristic are obtained at the same time in the first time period, and wherein the one or more pressure measurements in the set of first location pressure measurements associated with the identified first trailing characteristic and the one or more pressure measurements in the set of second location pressure measurements associated with the identified second trailing characteristic are obtained at the same time in the first time period.

4. The method of claim 1, wherein the identified first leading characteristic and the identified second leading characteristic are a characteristic type selected from the group of characteristic types consisting of: a maximum pressure measurement, a minimum pressure measurement, a maximum decreasing pressure measurement rate of change, and a maximum increasing pressure measurement rate of change.

5. The method of claim 4, wherein the identified first trailing characteristic and the identified second trailing characteristic are a characteristic type selected from the group of characteristic types consisting of: a maximum pressure measurement, a minimum pressure measurement, a maximum decreasing pressure measurement rate of change, and a maximum increasing pressure measurement rate of change.

6. The method of claim 5, wherein calculating the pressure ratio comprises using i) an average of a) one pressure measurement in the set of first location pressure measurements between the identified first leading characteristic and the identified first trailing characteristic and b) another pressure measurement in the set of first location pressure measurements between the identified first leading characteristic and the identified first trailing characteristic, and ii) an average of a) one pressure measurement in the set of second location pressure measurements between the identified second leading characteristic and the identified second trailing characteristic and b) another pressure measurement in the set of second location pressure measurements between the identified second leading characteristic and the identified second trailing characteristic.

7. The method of claim 5, 
wherein the identified first leading characteristic, the identified first trailing characteristic, the identified second leading characteristic, and the identified second trailing characteristic are a maximum pressure measurement, the first leading characteristic and the second leading characteristic being a maximum pressure measurement within a first predefined time interval of the first time period and the first trailing characteristic and the second trailing characteristic being a maximum pressure within a second predefined time interval of the first time period, and wherein the pressure ratio is calculated using i) a pressure measurement a first distance between the identified first leading characteristic and the identified first trailing characteristic and ii) a pressure measurement the first distance between the identified second leading characteristic and the identified second trailing characteristic.

8. The method of claim 7, wherein the first distance is midway between the identified first leading characteristic and the identified first trailing characteristic and midway between the identified second leading characteristic and the identified second trailing characteristic.

9. The method of claim 5,
wherein the identified first leading characteristic, the identified first trailing characteristic, the identified second leading characteristic, and the identified second trailing characteristic are a minimum pressure measurement, the first leading characteristic and the second leading characteristic being a minimum pressure measurement within a first predefined time interval of the first time period and the first trailing characteristic and the second trailing characteristic being a minimum pressure within a second predefined time interval of the first time period, and wherein the pressure ratio is calculated using i) a pressure measurement a first distance between the identified first leading characteristic and the identified first trailing characteristic and ii) a pressure measurement the first distance between the identified second leading characteristic and the identified second trailing characteristic.

10. The method of claim 5,
wherein the identified first leading characteristic, the identified first trailing characteristic, the identified second leading characteristic, and the identified second trailing characteristic are a maximum decreasing pressure measurement rate of change, the first leading characteristic and the second leading characteristic being a maximum decreasing pressure measurement rate of change within a first predefined time interval of the first time period and the first trailing characteristic and the second trailing characteristic being a maximum decreasing pressure measurement rate of change within a second predefined time interval of the first time period, and
wherein the pressure ratio is calculated using i) a pressure measurement a first distance between the identified first leading characteristic and the identified first trailing characteristic and ii) a pressure measurement the first distance between the identified second leading characteristic and the identified second trailing characteristic.

11. The method of claim 5,
wherein the identified first leading characteristic, the identified first trailing characteristic, the identified second leading characteristic, and the identified second trailing characteristic are a maximum increasing pressure measurement rate of change, the first leading characteristic and the second leading characteristic being a maximum increasing pressure measurement rate of change within a first predefined time interval of the first time period and the first trailing characteristic and the second trailing characteristic being a maximum increasing pressure measurement rate of change within a second predefined time interval of the first time period, and
wherein the pressure ratio is calculated using i) a pressure measurement a first distance between the identified first leading characteristic and the identified first trailing characteristic and ii) a pressure measurement the first distance between the identified second leading characteristic and the identified second trailing characteristic.

12. The method of claim 5,
wherein the first time period includes a first predefined time interval and a second predefined time interval, the second predefined time interval being subsequent to the first predefined time interval,
wherein the set of first location pressure measurements form a first location pressure waveform, the first location pressure waveform including a first cycle of first location pressure measurements over the first predefined time interval and a second cycle of first location pressure measurements over the second predefined time interval, and
wherein the set of second location pressure measurements form a second location pressure waveform, the second location pressure waveform including a first cycle of second location pressure measurements over the first predefined time interval and a second cycle of second location pressure measurements over the second predefined time interval.

13. The method of claim 12, wherein the first cycle corresponds to a first cardiac cycle and the second cycle corresponds to a second cardiac cycle.

14. The method of claim 12,
wherein the identified first leading characteristic is associated with one or more pressure measurements in the first cycle of first location pressure measurements and the identified first trailing characteristic is associated with one or more pressure measurements in the second cycle of first location pressure measurements,
wherein the identified second leading characteristic is associated with one or more pressure measurements in the first cycle of second location pressure measurements and the identified second trailing characteristic is associated with one or more pressure measurements in the second cycle of second location pressure measurements, and further comprising:
identifying a third leading characteristic associated with one or more pressure measurements in the second cycle of first location pressure measurements and a fourth leading characteristic associated with one or more pressure measurements in the second cycle of second location pressure measurements; and
identifying a third trailing characteristic associated with one or more pressure measurements in a third cycle of first location pressure measurements over a third predefined time interval of the first time period and a fourth trailing characteristic associated with one or more pressure measurements in a third cycle of second location pressure measurements over the third predefined time interval, wherein the identified third trailing characteristic is after the identified third leading characteristic in the set of first location pressure measurements and the identified fourth trailing characteristic is after the identified fourth leading characteristic in the set of second location pressure measurements.

15. The method of claim 14, wherein calculating the pressure ratio comprises using i) an average of a) a pressure measurement in the first cycle of first location pressure measurements between the identified first leading characteristic and the identified first trailing characteristic and b) a pressure measurement in the second cycle of first location pressure measurements between the identified third leading characteristic and the identified third trailing characteristic, and ii) an average of a) a pressure measurement in the first cycle of second location pressure measurements between the identified second leading characteristic and the identified second trailing characteristic and b) a pressure measurement in the second cycle of second location pressure measurements between the identified fourth leading characteristic and the identified fourth trailing characteristic.

16. The method of claim 15, wherein the identified first leading characteristic, the identified first trailing characteristic, the identified second leading characteristic, the identified second trailing characteristic, the identified third leading characteristic, the identified third trailing characteristic, the identified fourth leading characteristic, and the identified fourth trailing characteristic a maximum pressure measurement.

17. The method of claim 16, wherein the pressure ratio is calculated using i) the average of a) the pressure measurement in the first cycle of first location pressure measurements that is midway between the identified first leading characteristic and the identified first trailing characteristic and b) the pressure measurement in the second cycle of first location pressure measurements that is midway between the identified third leading characteristic and the identified third trailing characteristic, and ii) the average of a) the pressure measurement in the first cycle of second location pressure measurements that is midway between the identified second leading characteristic and the identified second trailing characteristic, and b) the pressure measurement in the second cycle of second location pressure measurements that is midway between the identified fourth leading characteristic and the identified fourth trailing characteristic.

18. The method of claim 1, further comprising the step of:
determining if the set of first location pressure measurements and the set of second location pressure measurements satisfy a set of pre-check conditions; and
if the set of pre-check conditions is satisfied, calculating the pressure ratio.

19. The method of claim 18,
wherein the set of pre-check conditions comprises a minimum pressure measurement in the set of first location pressure measurements that is between 30 and 180 mmHg, a maximum pressure measurement in the set of first location pressure measurements that is between 40 and 200 mmHg, a minimum pressure measurement in the set of second location pressure measurements that is between −5 and 180 mmHg, a maximum pressure measurement in the set of second location pressure measurements that is between 10 and 200 mmHg, pulse pressure corresponding to the set of first location pressure measurements that is at least 10 mmHg, pulse pressure corresponding to the set of second location pressure measurements that is at least 5 mmHg, a maximum pressure measurement in the set of second location pressure measurements that is less than 108% of a maximum pressure measurement in the set of first location pressure measurements, a minimum pressure measurement in the set of second location pressure measurements that is less than 108% of a minimum pressure measurement in the set of first location pressure measurements, heart rate over the first time period that is between 40 and 300 beats per minute, and none of the heartbeats over the first time period vary by more than 30% from an average of each other heartbeats occurring during the first time period, and
wherein determining if the set of first location pressure measurements and the set of second location pressure measurements satisfy the set of pre-check conditions comprises determining that each of the conditions comprising the set of pre-check conditions is satisfied.

20. The method of claim 1, wherein the first location is on a first side of a stenosis in the vessel and the second location is on a second opposite side of the stenosis in the vessel.

\* \* \* \* \*